US012564349B2

(12) United States Patent
Raschke et al.

(10) Patent No.: US 12,564,349 B2
(45) Date of Patent: Mar. 3, 2026

(54) SYSTEMS FOR COMPARATIVE ANALYSIS OF CARDIAC INFORMATION

(71) Applicant: GE Precision Healthcare LLC, Wauwatosa, WI (US)

(72) Inventors: Elise Raschke, Milwaukee, WI (US); Brian W. Nantz, Wauwatosa, WI (US); Edmund A. Greaves, Brown Deer, WI (US); Brian Young, Slinger, WI (US); Gordon Ian Rowlandson, Fox Point, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 318 days.

(21) Appl. No.: 18/304,872

(22) Filed: Apr. 21, 2023

(65) Prior Publication Data

US 2024/0350069 A1 Oct. 24, 2024

(51) Int. Cl.
*A61B 5/366* (2021.01)
*A61B 5/00* (2006.01)

(52) U.S. Cl.
CPC ............ *A61B 5/366* (2021.01); *A61B 5/7425* (2013.01); *A61B 5/743* (2013.01); *A61B 5/7435* (2013.01)

(58) Field of Classification Search
CPC . A61B 5/7425; A61B 5/349; A61B 2576/023; A61N 1/36135
See application file for complete search history.

(56) References Cited

U.S. PATENT DOCUMENTS

| | | | |
|---|---|---|---|
| 7,751,875 | B2 | 7/2010 | Bojovic |
| 9,451,890 | B2 | 9/2016 | Gitlin |
| 2006/0258947 | A1 | 11/2006 | Olson |
| 2008/0107302 | A1 | 5/2008 | Zhou |
| 2011/0060234 | A1 | 3/2011 | Zhou |
| 2011/0251504 | A1 | 10/2011 | Tereshchenko |
| 2015/0133803 | A1 | 5/2015 | Gupta |
| 2017/0332929 | A1* | 11/2017 | Tereshchenko ...... A61N 1/3622 |
| 2020/0022591 | A1 | 1/2020 | Drakulic |
| 2022/0031223 | A1 | 2/2022 | Li |

OTHER PUBLICATIONS

EP application 24168282.2 filed Apr. 3, 2024—partial Search Report issued Oct. 1, 2024; 11 pages.
EP application 24168282.2 filed Apr. 3, 2024—extended Search Report issued Dec. 20, 2024; 13 pages.
Vuong Quoc C et al: "Rotation direction affects object recognition", Vision Research, vol. 44, No. 14, Jun. 1, 2004 (Jun. 1, 2004), pp. 1717-1730, XP055798443, Amsterdam.NL ISSN: 0042-6989, DOI: 10.1016/j.visres.2004.02.002.

* cited by examiner

*Primary Examiner* — Alyssa M Alter

(57) ABSTRACT

A system for comparative analysis of cardiac information including an electrocardiogram (ECG), a user interface, a memory storing instructions; and a processor configured to execute the instructions to: obtain a first set of ECG data from the ECG device, the first set of ECG data being measured from a patient during a first time period; obtain a second set of ECG data from the ECG device, the second set of ECG data being measured from the patient during a second time period distinct from the first time period; obtain a first three-dimensional (3D) object based on the first set of ECG data; obtain a second 3D object based on the second set of ECG data; and control the user interface to simultaneously display the first 3D object and the second 3D object on a same axis.

22 Claims, 17 Drawing Sheets

SYSTEMS FOR COMPARATIVE ANALYSIS OF CARDIAC INFORMATION

FIELD

Embodiments of the subject matter disclosed herein relate to analysis of cardiac information, and in particular to systems for comparative analysis of cardiac information.

BACKGROUND

The heart is a complex and essential organ that is responsible for pumping blood throughout the body. To study and understand the functioning of the heart, various medical imaging techniques have been developed, developed, including electrocardiogram (ECG) and echocardiogram. ECG is a non-invasive method for measuring the electrical activity of the heart and can be used to diagnose various heart conditions. One important aspect of ECG is the analysis of cardiac vector loops.

Cardiac vector loops are graphical representations of the electrical activity of the heart, which can provide valuable information about the heart's functioning. The loops are constructed by plotting the direction and magnitude of the electrical vectors of the heart at different points in time. They are used by medical professionals to diagnose and monitor heart conditions, such as arrhythmias, heart attacks, and other cardiac diseases.

BRIEF DESCRIPTION

According to an aspect of the disclosure, a system for comparative analysis of cardiac information may include an electrocardiogram (ECG) device comprising a plurality of electrodes and a monitor configured to measure electrical signals through the electrodes, the ECG device being configured to provide ECG data; a user interface configured to provide information to a user and obtain information from a user; a memory storing instructions; and a processor configured to execute the instructions to: obtain a first set of ECG data from the ECG device, the first set of ECG data being measured from a patient during a first time period; obtain a second set of ECG data from the ECG device, the second set of ECG data being measured from the patient during a second time period distinct from the first time period; obtain a first three-dimensional (3D) object based on the first set of ECG data; obtain a second 3D object based on the second set of ECG data; and control the user interface to simultaneously display the first 3D object and the second 3D object on a same axis.

According to another aspect of the disclosure, a system for comparative analysis of cardiac information may include a user interface configured to provide information to a user and obtain information from a user; a memory storing instructions; and a processor configured to execute the instructions to: control the user interface to display a plurality of icons corresponding to three-dimensional (3D) objects, each 3D object being obtained from a different set of ECG data, each set of ECG data being obtained during a distinct time period; control the user interface to display an xyz axis simultaneously with the plurality of icons; and responsive to selection of an icon, control the user interface to display a 3D object corresponding to the icon on the xyz axis. Multiple 3D objects may be simultaneously displayed on the xyz axis in response to multiple icons being selected.

According to yet another aspect of the disclosure, a method of displaying cardiac information may include obtaining a first set of ECG data, the first set of ECG data being measured from a patient during a first time period; obtaining a second set of ECG data, the second set of ECG data being measured from the patient during a second time period distinct from the first time period; obtaining a first three-dimensional (3D) object based on the first set of ECG data; obtaining a second 3D object based on the second set of ECG data; and simultaneously displaying the first 3D object and the second 3D object on a same axis.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

3

DETAILED DESCRIPTION

Figure 1:
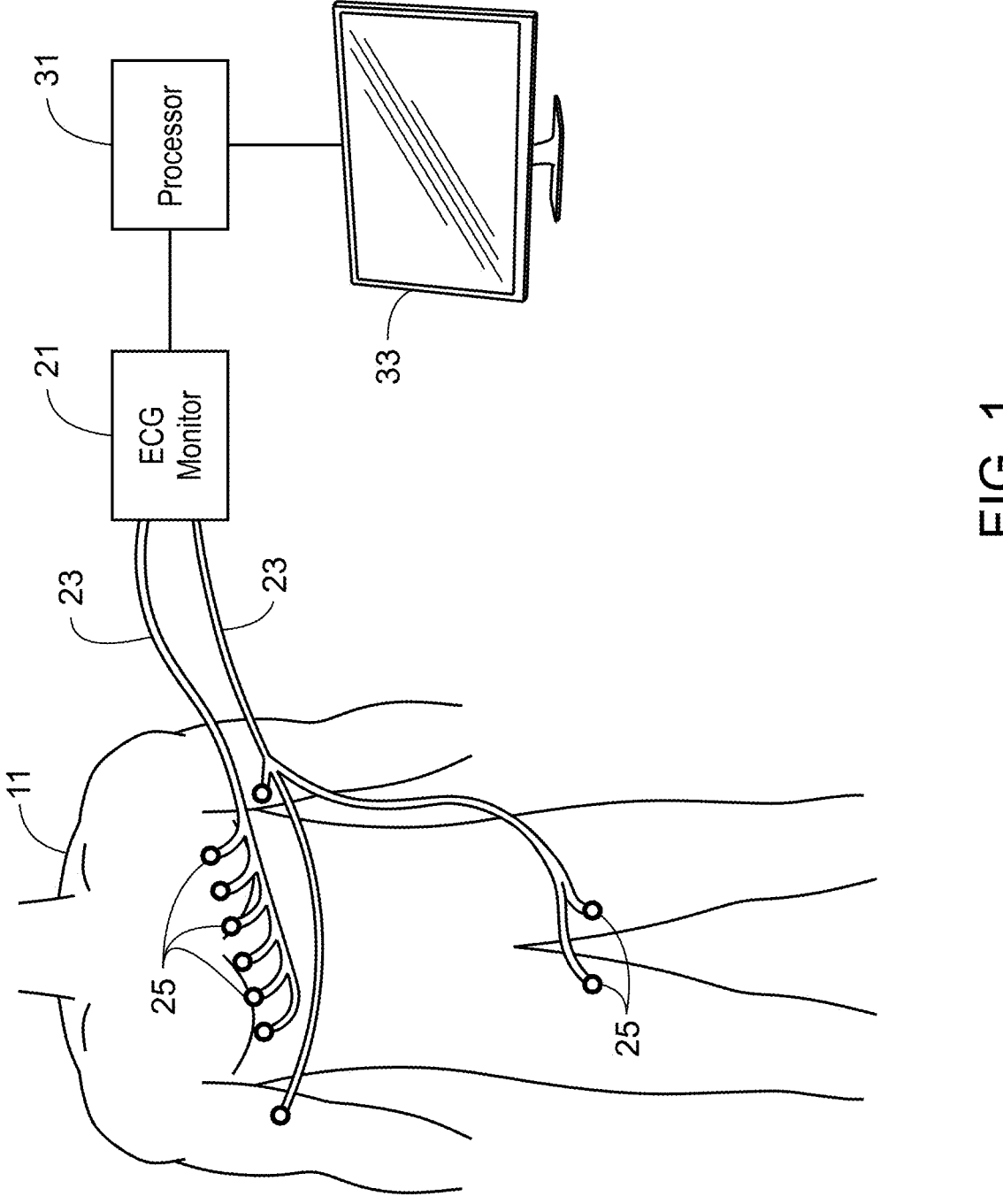
FIG. 1 is a diagram of a system for obtaining cardiac information from a patient, generating a three-dimensional representation of the information, and displaying the information to a medical professional, according to an embodiment.

The following detailed description of example embodiments refers to the accompanying drawings. The same reference numbers in different drawings may identify the same or similar elements.

The foregoing disclosure provides illustration and description, but is not intended to be exhaustive or to limit the implementations to the precise form disclosed. Modifications and variations are possible in light of the above disclosure or may be acquired from practice of the implementations.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more" or "at least one." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," "includes," "includes," "including," "comprises," "comprising," or the like are intended to be open-ended terms. Further, the phrase "based on" is intended to mean "based, at least in part, on" unless explicitly stated otherwise. References to "one embodiment" of the present invention are not intended to be interpreted as excluding the existence of additional embodiments that also incorporate the recited features. The terms "first," "second," and "third," etc. are used merely as labels, and are not intended to impose numerical requirements or a particular positional order on their objects.

The following description relates to various embodiments of systems and methods for obtaining and displaying cardiac information for comparative analysis.

Abnormalities in cardiac function can be detected by a clinician viewing cardiac data. Three-dimensional representation of cardiac information, such as cardiac vector loops, magnitude and angle of maximum vectors of the vector loops, and angles between maximum vectors of the vector loops (e.g. QRS-T angle), presents the cardiac information to the clinician in a form in which abnormalities can be quickly and easily comprehended. In many cases, abnormalities may be identified based on changes in a patient's cardiac information over time. By simultaneously displaying a patient's cardiac information from different times (e.g. ECG reading taking at 1 month intervals) in three dimensions on a same axis for comparative analysis, a practitioner is able to quickly and accurately diagnose a patient with a condition that may not be readily detectable through other methods of viewing the cardiac information.

FIG. 1 shows a system for obtaining cardiac information from a patient, generating a three-dimensional representation of the information, and displaying the information to a medical professional, according to an embodiment.

FIG. 1 shows an electrocardiogram (ECG) monitor connected to a patient 11. The ECG monitor 21 may be used to obtain cardiac information for a patient at separate time intervals. For example, the separate time intervals may be different visits to a medical office, preset time intervals such as a month, pre-operative versus post-operative, etc. According to an embodiment, separate ECG monitors may be used to obtained different ECG reading. For example, an at home 6 lead ECG monitor may be used for a first reading and a 12 lead ECG monitor may be used for a second reading taken at a doctor's office.

An electrocardiogram (ECG) is a medical test that measures the electrical activity of the heart. The ECG monitor 21 records the electrical signals generated by the heart as it beats.

During an ECG test, electrodes 25 are attached to the skin on the chest, arms, and legs. These electrodes 25 detect the electrical impulses that occur each time the heart beats. The ECG monitor 21 then amplifies and records these signals, producing a graph or waveform that shows the heart's electrical activity over time.

The waveform produced by an ECG represents the depolarization and repolarization of the heart's electrical activity during each heartbeat. The waveform is made up of several waves and intervals, each of which represents a different phase of the heart's electrical activity. The main waves on an ECG are the P wave, QRS complex, and T wave.

The P wave represents the depolarization of the atria (the upper chambers of the heart), the QRS complex represents the depolarization of the ventricles (the lower chambers of the heart), and the T wave represents the repolarization of the ventricles.

As shown in FIG. 1, the electrocardiogram may include a plurality of electrodes 25 attached to a patient 11. The electrodes 25 may be connected to an ECG monitor 21 through lead wires 23. The ECG monitor 21 may input raw data obtained from the electrodes 25 and output usable data indicating the electrical activity of the heart.

The data produced by the ECG monitor 21 may be processed by a processing module 31 to obtain cardiac vectors representing the electrical activity of the patient's 11 heart during the ECG measurement.

To obtain cardiac vectors, electrodes 25 are placed on the surface of the skin at specific locations around the chest and limbs. These electrodes 25 are connected to the ECG monitor 21, which records the electrical signals generated by the heart. The electrical signals are represented as waveforms on the ECG tracing. By analyzing the different waves and intervals on the ECG tracing, the direction and magnitude of the cardiac vectors can be obtained.

The direction of the cardiac vectors is determined by the sequence of electrical activation of the heart, which starts at the sinoatrial (SA) node in the right atrium and spreads through the atria and ventricles. The magnitude of the cardiac vectors is determined by the amplitude of the electrical signals recorded by the electrodes on the body surface. The greater the amplitude of the signal, the stronger the cardiac vector.

The processing module 31 may generate three-dimensional (3D) cardiac vector loops based on the cardiac vectors. The vector loops may be generated based on ECG data using methods known in the art.

Figure 2A:
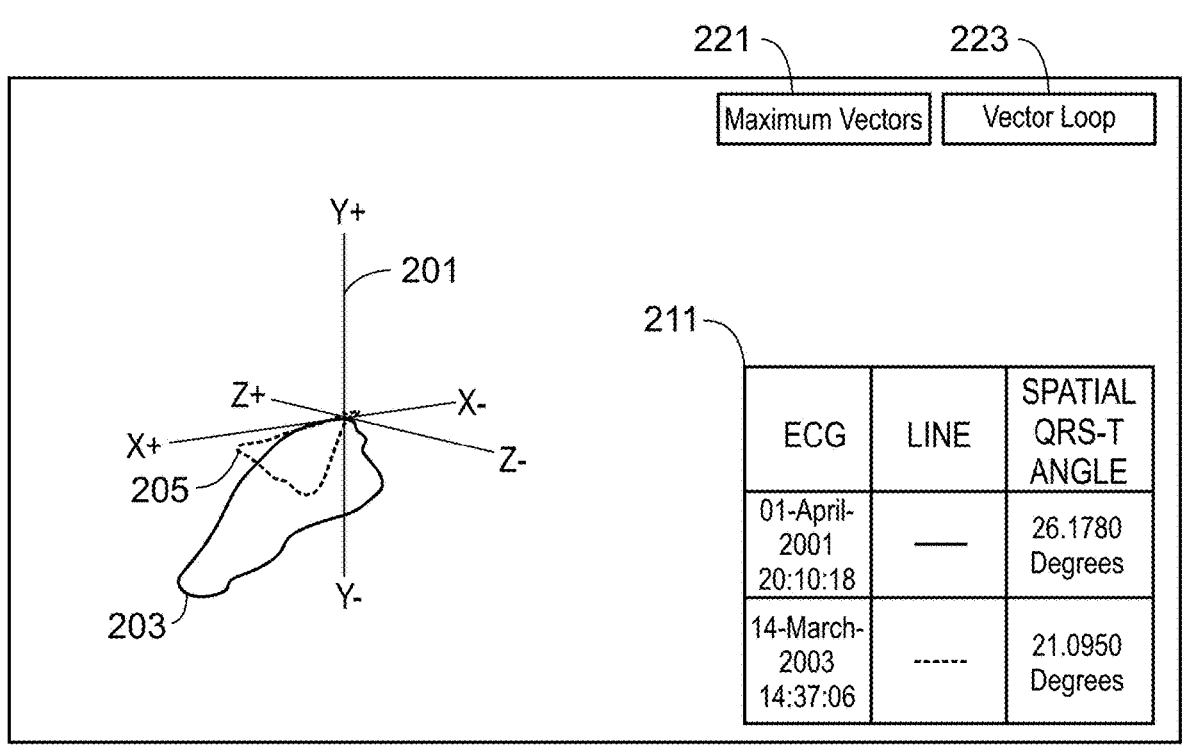
FIGS. 2A-2E show display outputs of multiple cardiac vector loops 203, 205 rendered in three dimensions on a same xyz axis for comparative analysis, according to an embodiment.
Figure 2B:
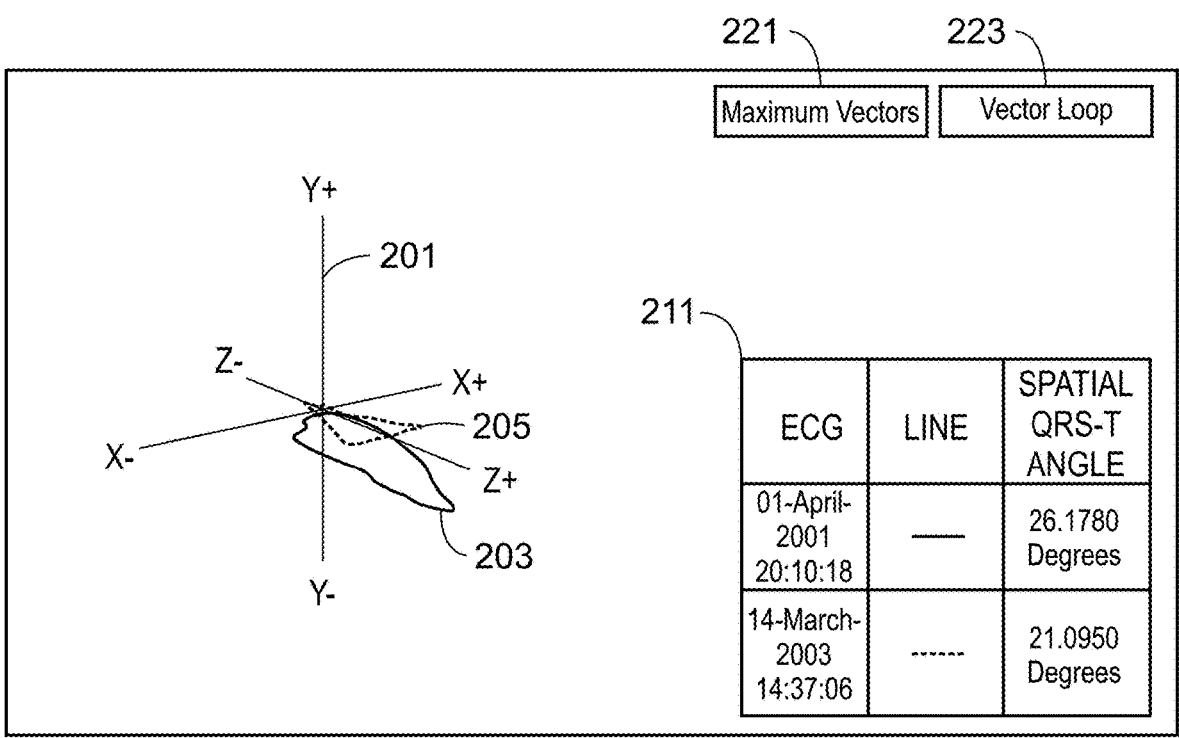
Figure 2C:
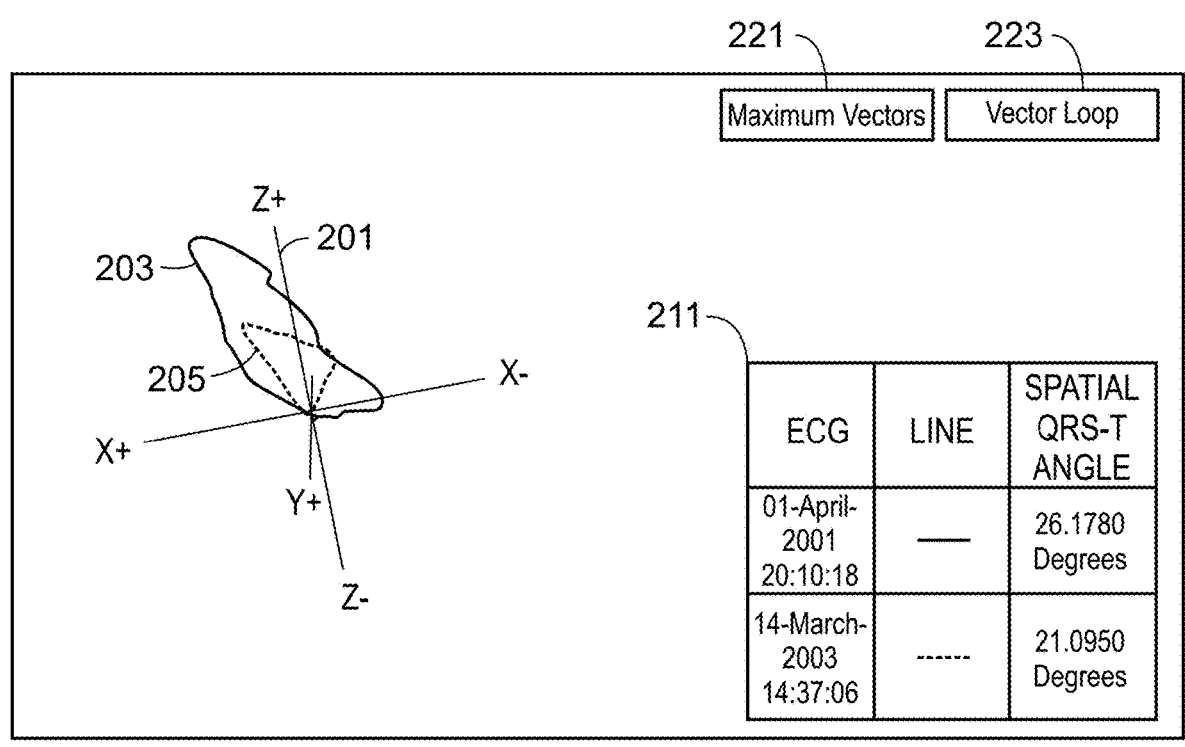
Figure 2D:
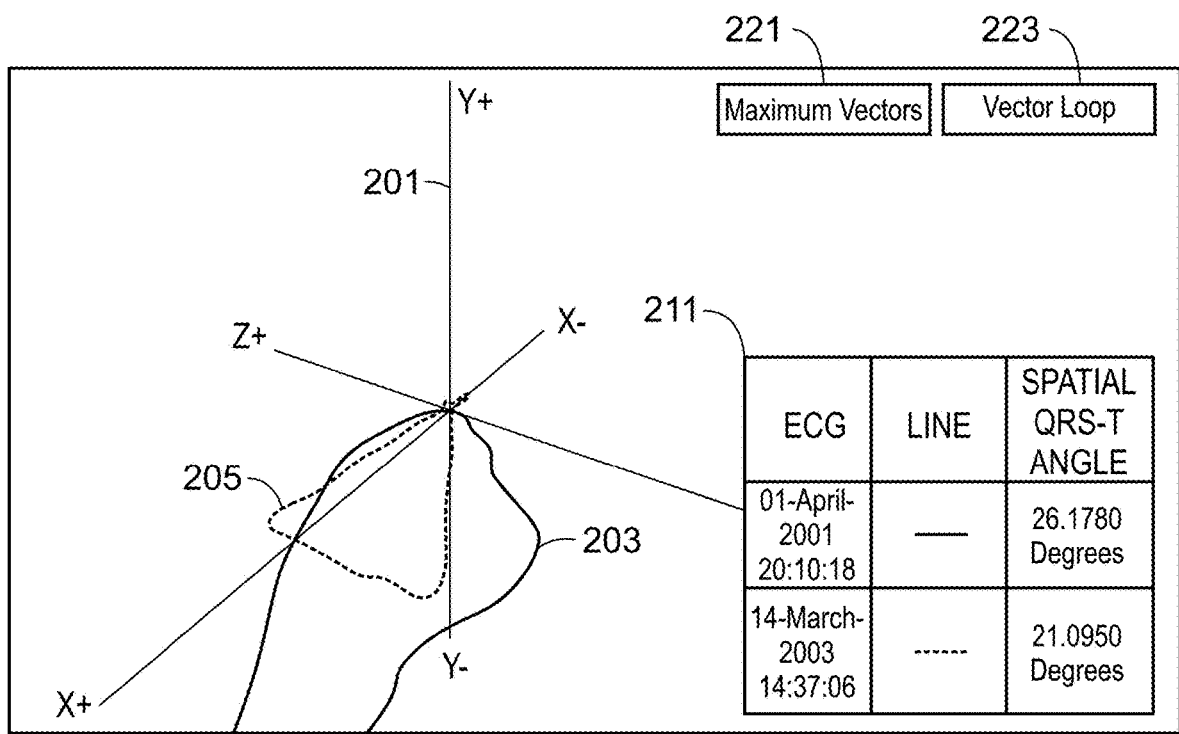
Figure 2E:
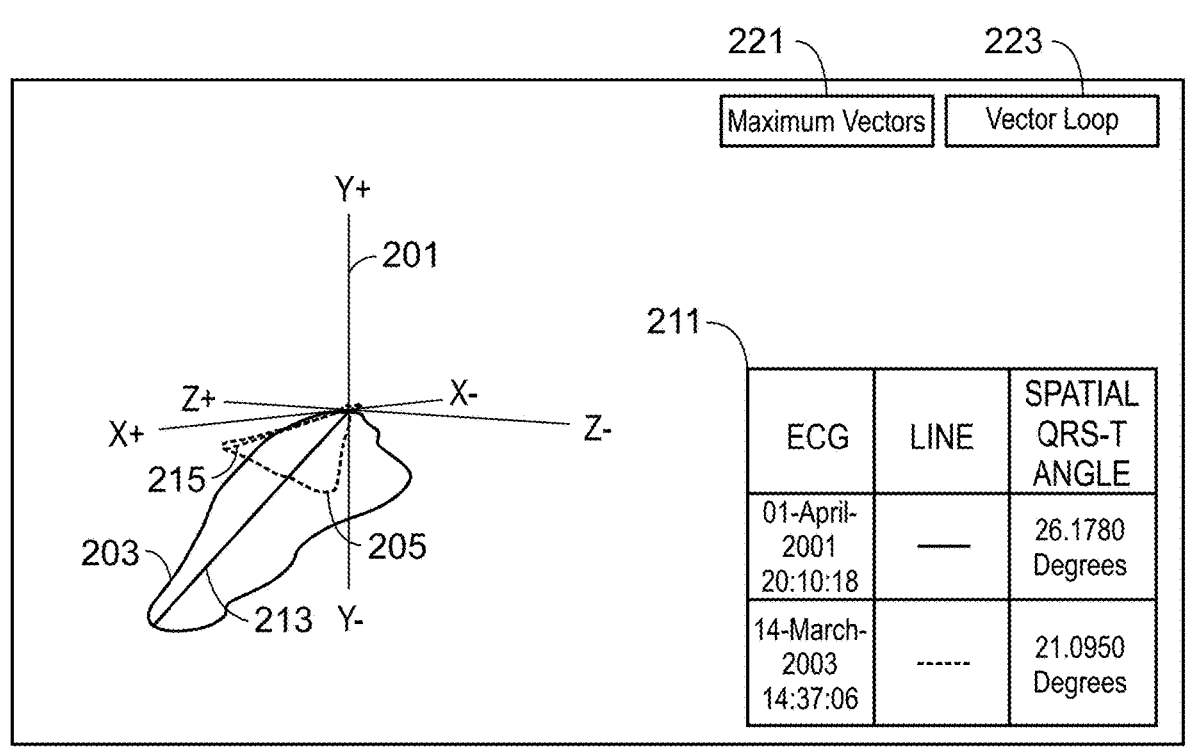

FIGS. 2A-2E show a display output of multiple cardiac vector loops 203, 205 rendered in three dimensions on a same xyz axis 201 for comparative analysis, according to an embodiment. FIG. 2A shows two cardiac vector loops 203, 205 from a first point of view, according to an embodiment. FIG. 2B shows the cardiac vector loops 203, 205 when viewed from a second point of view due to rotation of the loops around the y-axis, according to an embodiment. FIG. 2C shows the cardiac vector loops 203, 205 when viewed from a third point of view due to rotation of the loops around the x-axis, according to an embodiment. FIG. 2D show a zoomed in view of the cardiac vector loops 203, 205, according to an embodiment. FIG. 2E shows the two cardiac vector loops 203, 205 along with maximum vectors lines 213 and 215 for each loop.

As shown in legend 211 of FIGS. 2A-2E, a first cardiac vector loop 203 (solid line) is based on an ECG taken Apr. 1, 2001. The first cardiac vector loop 203 is shown in FIGS. 2A-2E is a QRS loop, but the disclosure is not limited to this particular loop. FIGS. 2A-E also show a second cardiac vector loop 205 (dashed line) based on an ECG taken Mar. 14, 2003. The second cardiac vector loop 205 is shown in FIGS. 2A-2E is a QRS loop, but the disclosure is not limited to this particular loop. As shown in FIGS. 2A-E, the first cardiac vector loop 203 and the second cardiac vector loop 205 are simultaneously displayed in three dimensions on the same xyz axis 201. The vector loops 203, 205 may be generated based on the ECG data using methods known in the art. The vectors loops 203, 205 may be based on a single heartbeat or an average of multiple heart beats.

According to an embodiment, y-z plane of the displayed axis 201 may be aligned with the coronal plane of the patient, the z-x plane of the axis 201 may be aligned with the transverse plane of the patient, and the y-x plane of the axis 201 may be aligned with the sagittal plane of the patient. Based on these preset alignments, a medical professional will be able quickly ascertain how the vector loops are spatially related to the patient's body. As such, each of the vector loops may be aligned with these planes.

The orientation of the vector loops 203, 205 may be affected by the placement of the ECG electrodes on the patient. Differences in electrode placement may cause there to be differences in the displayed vector loops which are not caused by cardiac changes, but are rather due to inconsistencies in the measurement. According to an embodiment, a first vector loop may be aligned with the planes as discussed above and following vector loops may be aligned with the first vector loop. For example, the vector loops may be aligned by aligning their maximum vectors. By aligning the vector loops with each other rather than with the xyz axis, differences in the vector loops due to measurement inconsistencies may be minimized.

According to an implementation, vector loops from multiple ECGs may be aligned based on mean vectors for one or more of the P-wave, QRS and T-wave. If the P-wave, QRS and T-wave have roughly the same angles between them on one ECG versus a prior, then the clinical state of the heart may be the same. The vector loops may be overlayed so that there is maximum alignment of the three mean vectors and the angles between them. Once this is done, an inverse transform may be applied back to the 12-lead ECG data to shows what it would look like after the alignment step.

As shown in FIG. 2A, a legend 211 including information corresponding to the vector loops 203, 205 may be displayed along with the vector loops 203, 205 for informing the practitioner of information associated with the loops. The legend 211 may include information such as the date on which the ECG was taken as well as sizes and angles of vectors associated with the vector loops. For example, as shown in FIG. 2A, the spatial QRS-T angle is shown because this angle provides valuable insights to a medical professional interpreting the displayed information. The disclosure is not limited to the above describe embodiment, any measurement standard known in the art for measurement of vectorcardiography may be displayed in the legend. The legend 211 may also include characteristic identifying the loop. As shown in FIG. 2A, the first loop is identified by a solid line and the second loop is identified by a dashed line. Other method for identifying the separate loops may be used, such as different colors.

As shown in FIGS. 2B and 2C, a point of view from which the vector loops 203, 205 and xyz axis 201 are displayed may be adjusted by a user. According to an embodiment, a user may click and drag with the mouse cursor to rotate the xyz axis 201 and vector loops 203, 205. According to other embodiments, a user may drag their finger across the screen or select a directional icon to change the point of view from which the vectors loops 203, 205 and axis 201 are displayed. According to other embodiments, known methods may be used to adjust the point of the from which the vector loops 203,205 and xyz axis 201 is displayed.

As seen when comparing FIGS. 2A and 2B, the vector loops 203, 205 may be rotated around the y-axis when dragging the cursor horizontally. As seen when comparing FIGS. 2A and 2C, the vector loops 203, 205 and xyz axis 201 may be rotated around the x and/or z axes when the cursor is dragged vertically.

As seen when comparing FIG. 2A to FIG. 2D, a user may zoom in on the vector loops 203, 205 and the xyz axis 201. Zooming may be performed by methods known in the art, such as scrolling a wheel on a mouse or dragging two fingers together/apart.

As shown in FIG. 2E, maximum vectors 213, 215 for each vector loop 203, 205 may be displayed along with the vector loops 203, 205. Displaying of the maximum vectors 213, 215 and vector loops 203, 205 may be toggled by selecting displayed icons 221, 223. According to an embodiment, the maximum vectors 213, 215 (also referred to as maximum instantaneous vector) may be based on a summation of one or more vectors, such as a summation of all vectors that make the vector loop. According to another embodiment, the maximum vectors may be a single largest vector of the vectors that make up the vector loop.

FIGS. 3A-3E show a display output of cardiac information, obtained from multiple ECG recordings, in three dimensions on a same axis for comparative analysis, according to an embodiment. The point of view from which the cardiac information and xyz axis 301 is displayed may be controlled in a similar manner as discussed above with respect to FIGS. 2A-E.

Figure 3A:
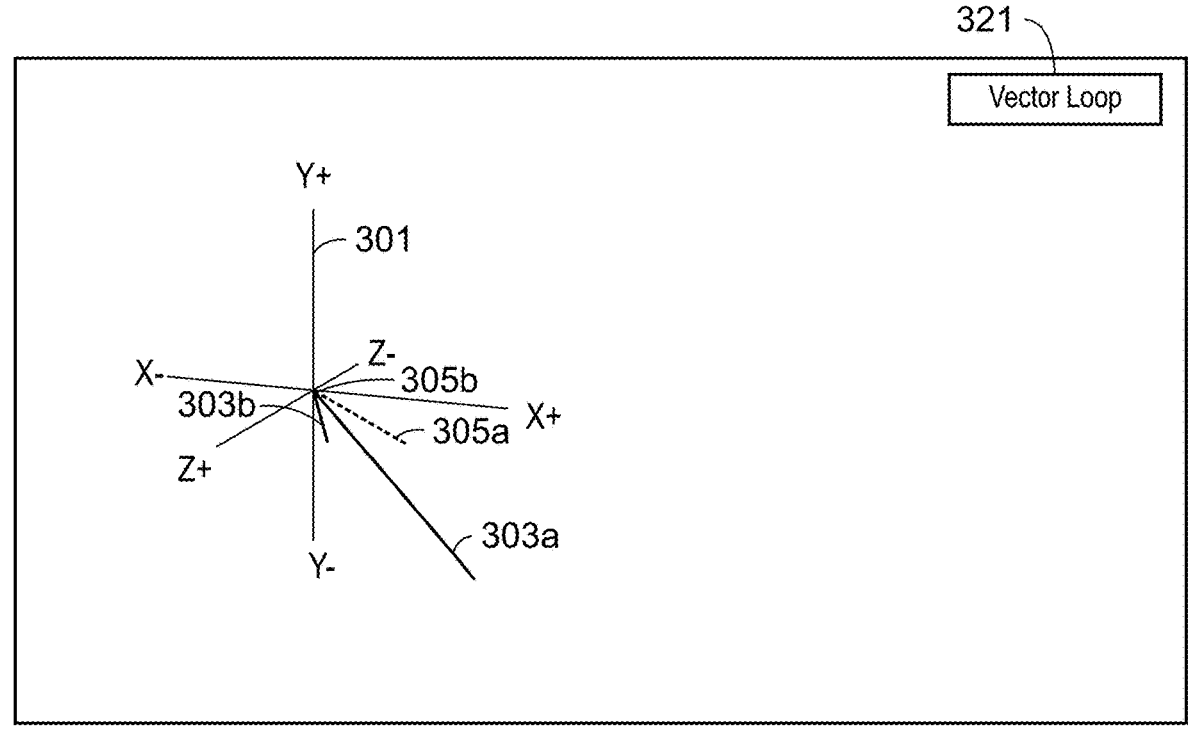
FIGS. 3A-3E show display outputs of cardiac information, obtained from multiple ECG recordings, in three dimensions on a same axis for comparative analysis, according to an embodiment.

As shown in FIG. 3A, a maximum QRS vector 303a and a maximum T vector 303b (solid lines) are shown for a first ECG recording and a maximum QRS vector 305a and a maximum T vector 305b (dashed lines) are shown for a second ECG recording. As such, the QRS-T angle for each ECG recording is shown between the vectors.

Figure 3B:
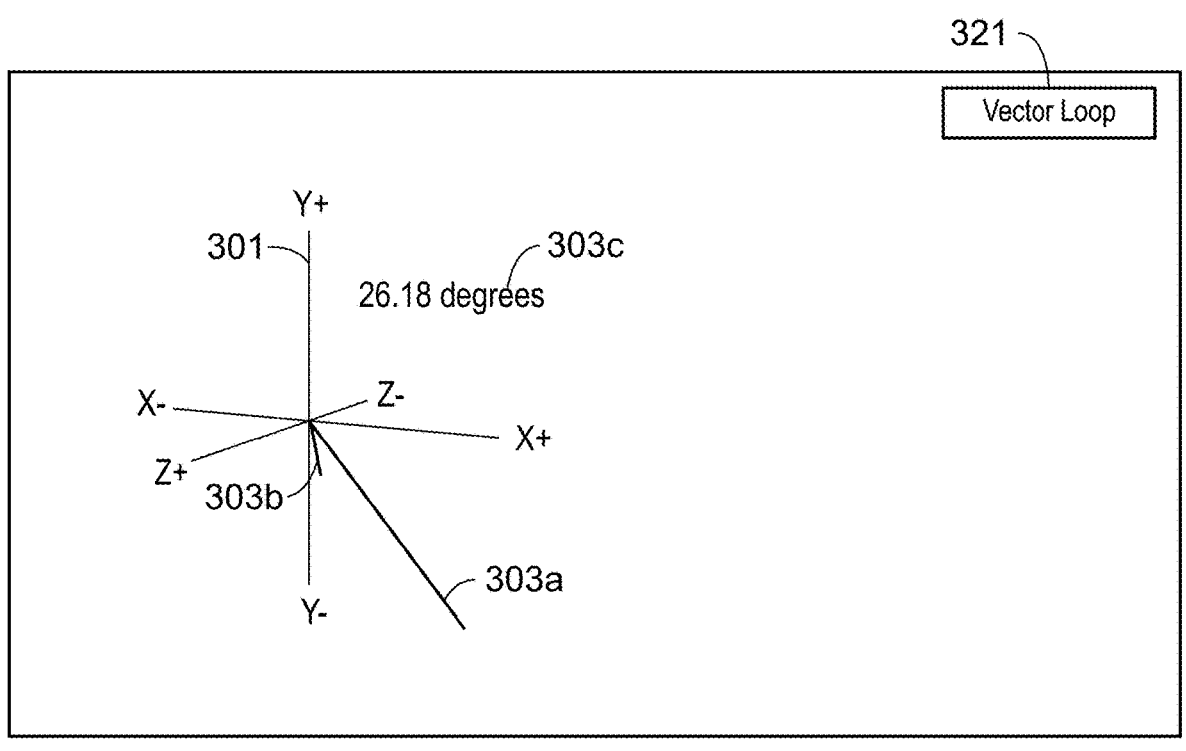
Figure 3C:
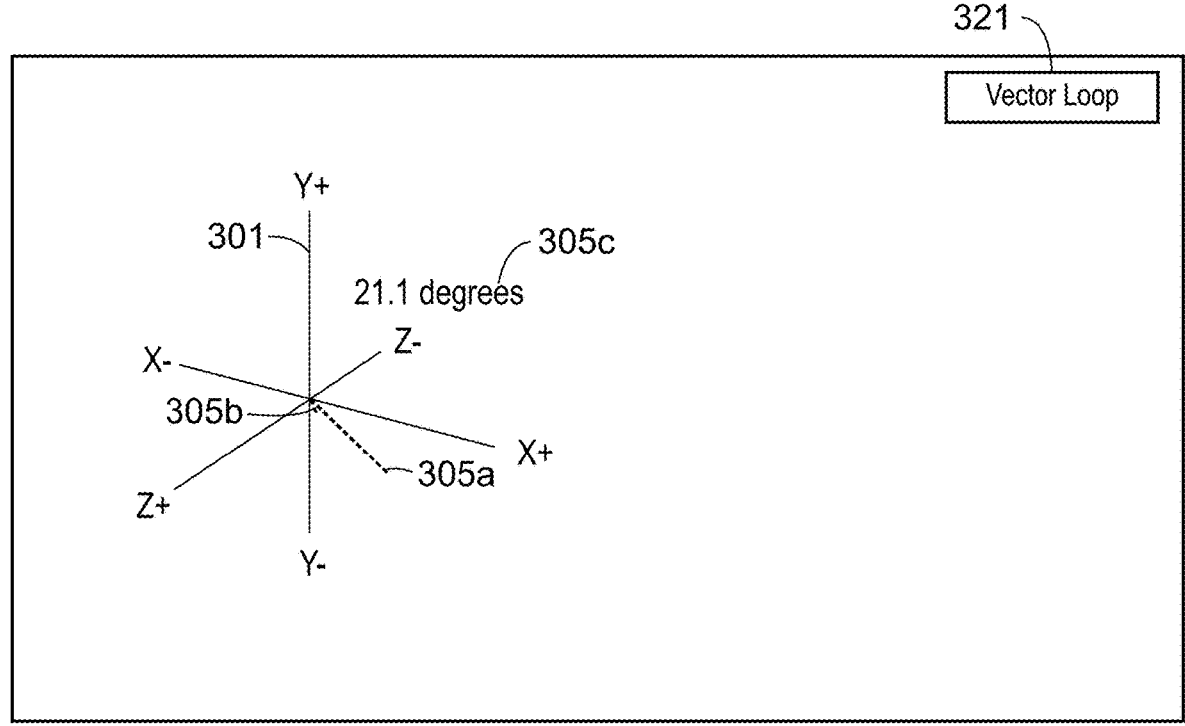

Text of the exact QRS-T angle may be displayed when a user selects a vector from one of the ECG recordings. As shown in FIG. 3B, when a maximum vector 303*a*, 303*b* of the first ECG recording is selected, the maximum vectors 305*a*, 305*b* from the second ECG are removed and text 303*c* specifying the exact QRS-T angle of the first ECG recording is displayed. As shown in FIG. 3C, when a maximum vector 305*a*, 305*b* of the second ECG recording is selected, the vectors 303*a*, 303*b* from the first ECG are removed and text 305*c* specifying the exact QRS-T angle is displayed.

According to an implementation, a vector representing the ventricular gradient may be displayed for each ECG. For example, in response to selection of an icon, a vector representing the ventricular gradient may be displayed with the cardiac loop, the maximum vectors, and/or by itself. The vector representing the ventricular gradient may be obtained by summing of an integral of the max QRS vector and an integral of the max T wave vector.

Figure 3D:
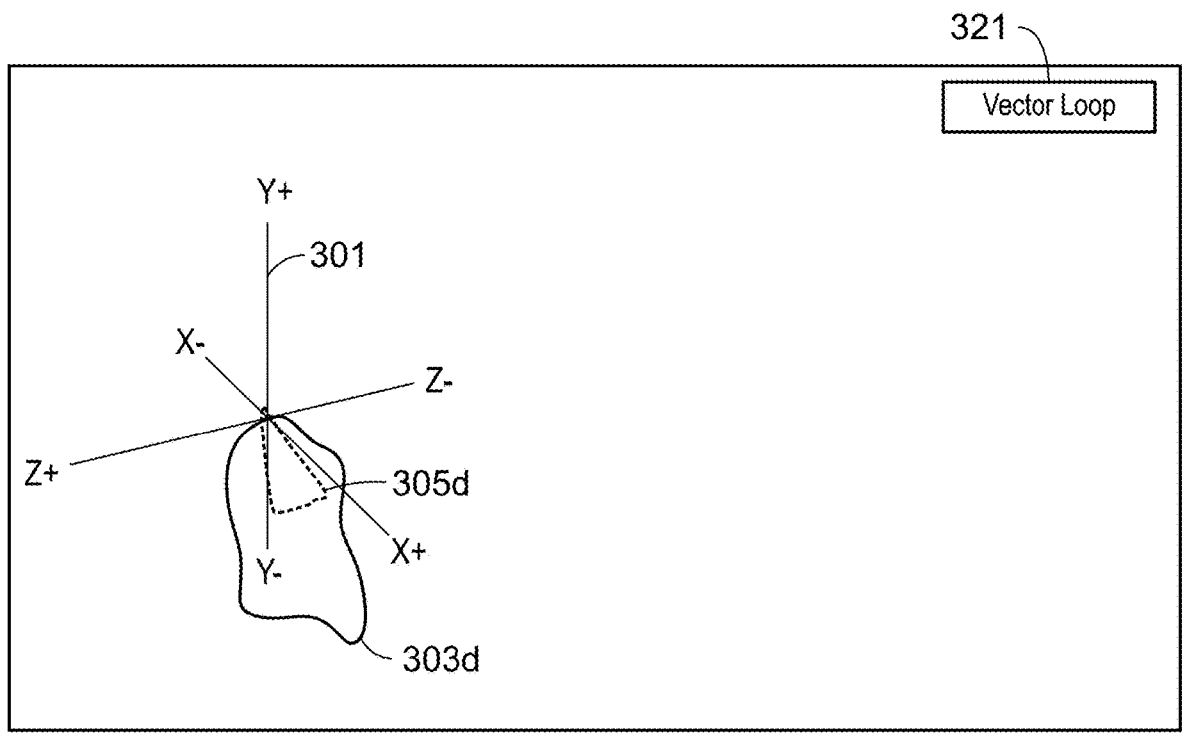
Figure 3E:
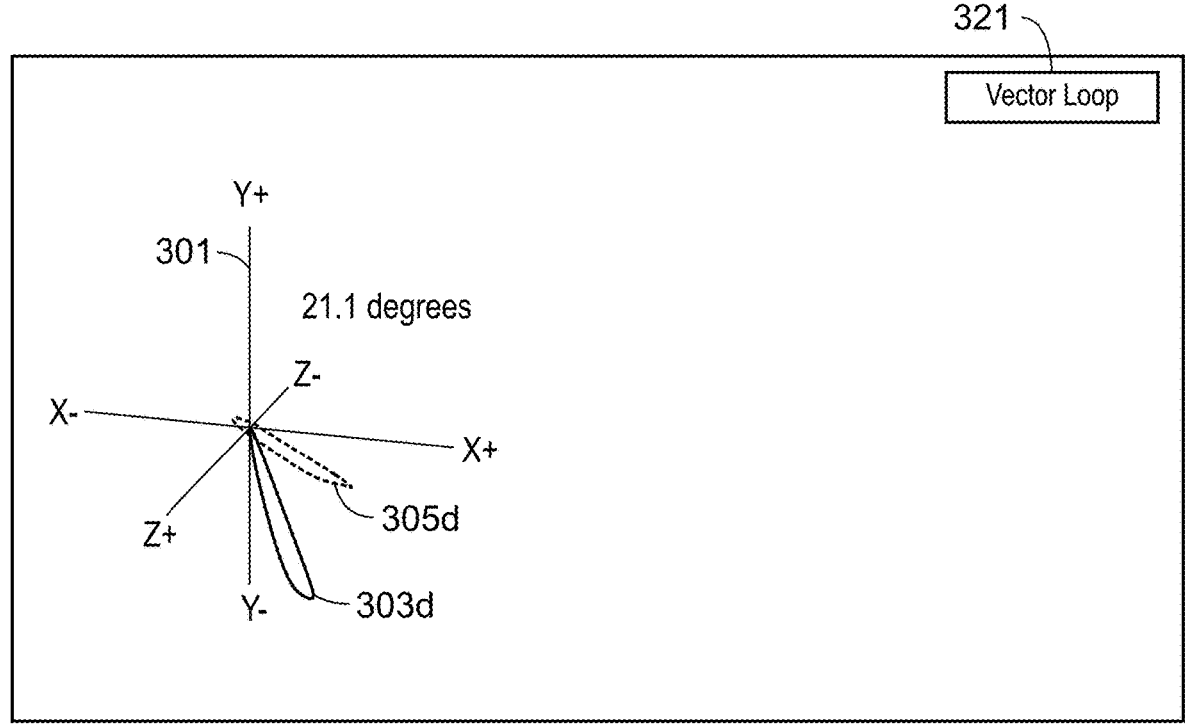

As shown in FIG. 3D, the vector loops 303*d*, 305*d* may be displayed in response to a user input, such as selecting icon 321. As shown in FIG. 3E, selection of a vector loop when the icon 321 has already been selected may display the QRS-T angle of the selected vector loop along with the vector loops.

In FIGS. 2A-E and 3A-E, cardiac information from two ECGs is simultaneously displayed for explanatory purposes. Other embodiment may display cardiac information from more than two ECGs. For example, three vector loops and maximum vector may be simultaneously displayed. The amount of cardiac information displayed may be based on a selection of a user. For example, a user may select 3 or more ECGs from a list for simultaneous viewing.

Figure 4:
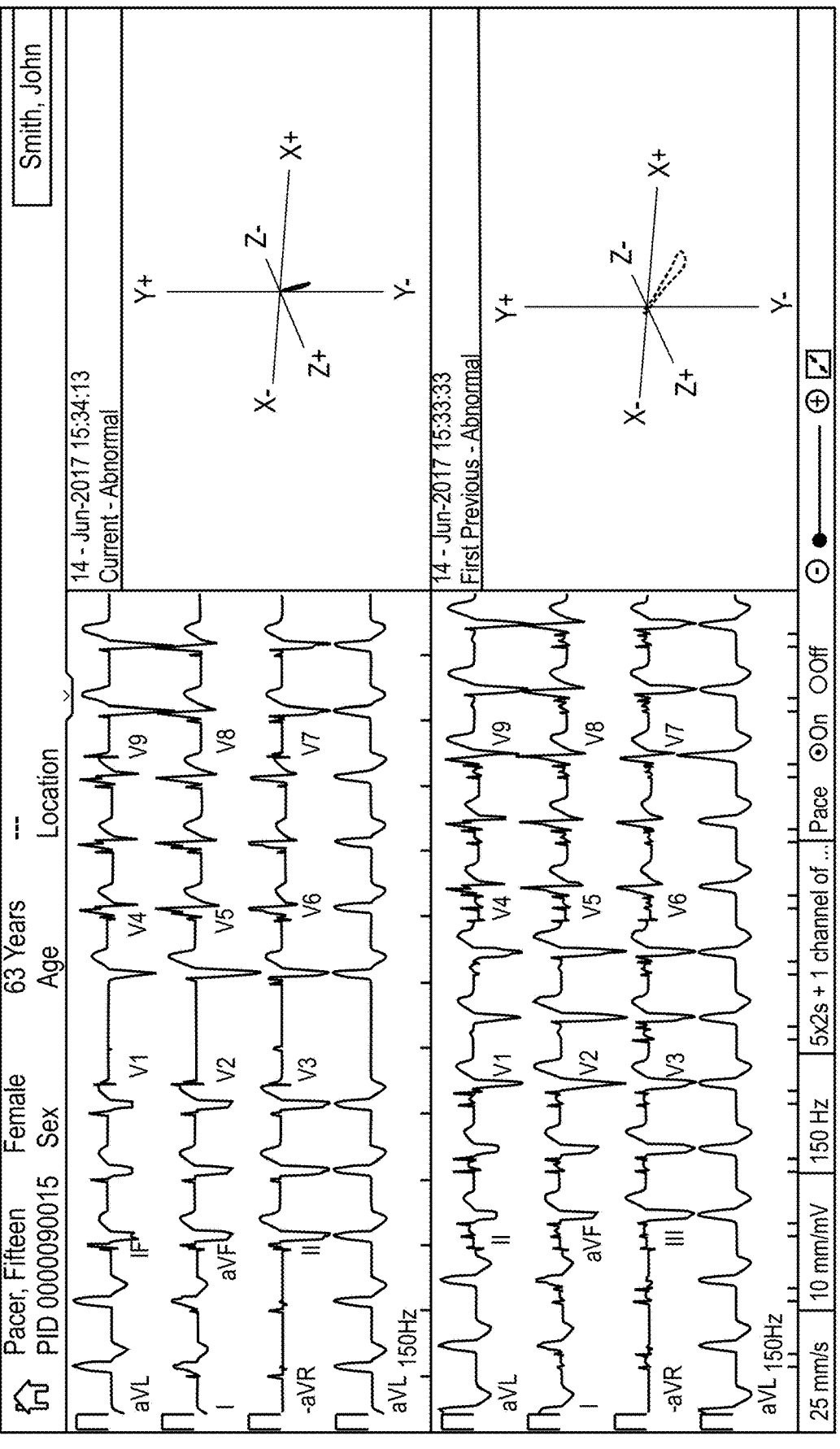
FIG. 4 shows a user interface for comparative analysis of cardiac data, according to an embodiment.

FIG. 4 shows a user interface for comparative analysis of cardiac data, according to an embodiment As shown in FIG. 4, cardiac information obtained from a first ECG recording (top) and cardiac information obtained from a second ECG recording (bottom) is simultaneously output for comparative analysis. For each ECG, the cardiac information may be provided in graphical form indicating a voltage of each lead over a period of time (left side) and in three-dimensional form (right side). The three-dimensional representations of the cardiac information may be provided and manipulated in a manner similar to FIGS. 2A-E and 3A-E.

For example, a medical professional may select a first ECG taken at a first time and a second ECG taken a second time removed from the firs time (e.g. 1 month apart) for analysis when diagnosing the patient. Cardiac information from the selected ECGs may be displayed as shown in FIG. 4 for comparative analysis. While FIG. 4 shows cardiac information from 2 ECGs being displayed, displaying cardiac information from more than two ECGs is within the scope of this disclosure.

According to an embodiment, the multiple vector loops may be displayed on a same axis rather then on different axes as shown in FIG. 4. That is, the ECG waveforms may separately be displayed on the screen along with the associated vector loops and associated cardiac information on a single axis. Display of the vector loops and associated cardiac information may be manipulated in a similar manner as discussed above with respect to FIGS. 2A-E and 3A-E.

Figure 5:
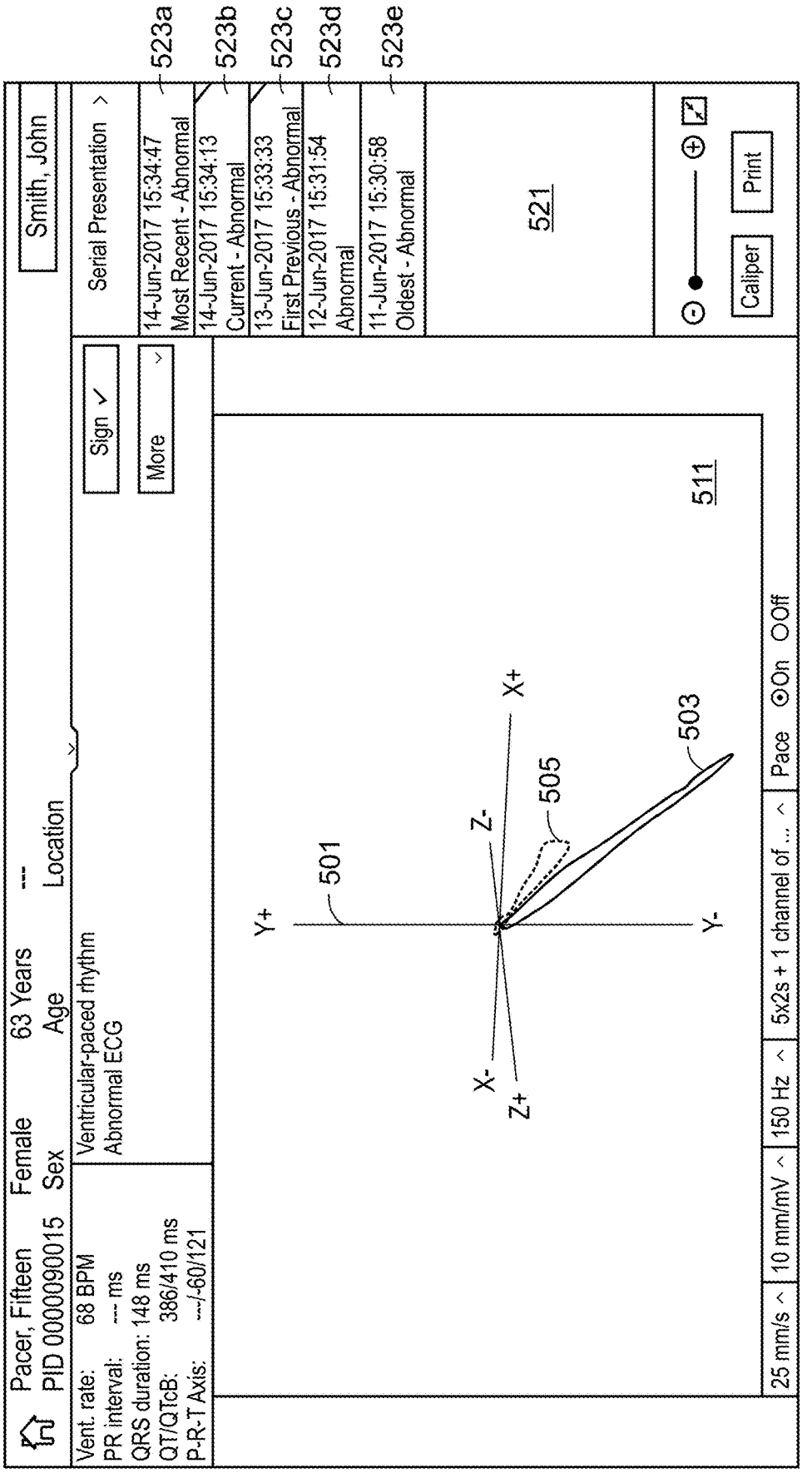
FIG. 5 shows a user interface for comparative analysis of cardiac information, according to an embodiment.

FIG. 5 shows a user interface for comparative analysis of cardiac information, according to an embodiment.

As shown in FIG. 5, the user interface may include a selection window 521 including multiple icons 523*a*-523*e* corresponding to multiple ECG recordings taken at separated intervals. Information identifying each ECG may be included each icon 523*a*-523*e*. As shown in FIG. 5, a time at which the ECG was taken may be included in each icon 523*a*-523*e*. The icons 523*a*-523*e* may also indicate whether the ECG was normal or abnormal, as well as if the ECG was taken before or after a procedure.

In a 3D display window 511. 3D vector loops 503, 505 may be displayed on an xyz axis 501 for each selected ECG 523*b*, 523*c*. The 3D display window 511 may display cardiac information and may be controlled in a similar manner as discussed with respect to FIGS. 2A-E and 3A-E.

For example, as shown in FIG. 5, a user may select a first ECG icon 523*b* representing an ECG from 15:34:13 on Jun. 14, 2017 and a second ECG icon 523*c* representing and ECG from 15:33:33 on Jun. 13, 2017 for comparative analysis. In response to the selections, 3D cardiac vector loops 503, 505 corresponding to the selected ECGs may be simultaneously displayed. The 3D information may be presented and controlled in a similar manner as discussed with respect to FIGS. 2A-F and 3A-E. According to some embodiments, selection of an ECG may cause vector loops, maximum vectors, and/or angles between maximum vectors corresponding to the ECG to be displayed.

As discussed above, three-dimensional representation of cardiac information presents the cardiac information to the clinician in a form in which abnormalities can be quickly and easily comprehended. In many cases, abnormalities in cardiac function can be identified by comparing data data from multiple sources. For example, ECG data provides insights on the electrical activity of the heart and echocardiogram data provides insights on the mechanical activity of the heart. A presence of electrical activity without a corresponding muscle contraction (mechanical activity) can indicate a cardiac condition. As such, certain cardiac conditions may be readily apparent to a medical professional through comparative analysis of electrical and mechanical cardiac data. Additionally, viewing the electrical and mechanical aspects of the heart simultaneously, clinicians can view wall motion, apply the clinical intervention, and then see the electrical changes of the therapy.

Figure 6:
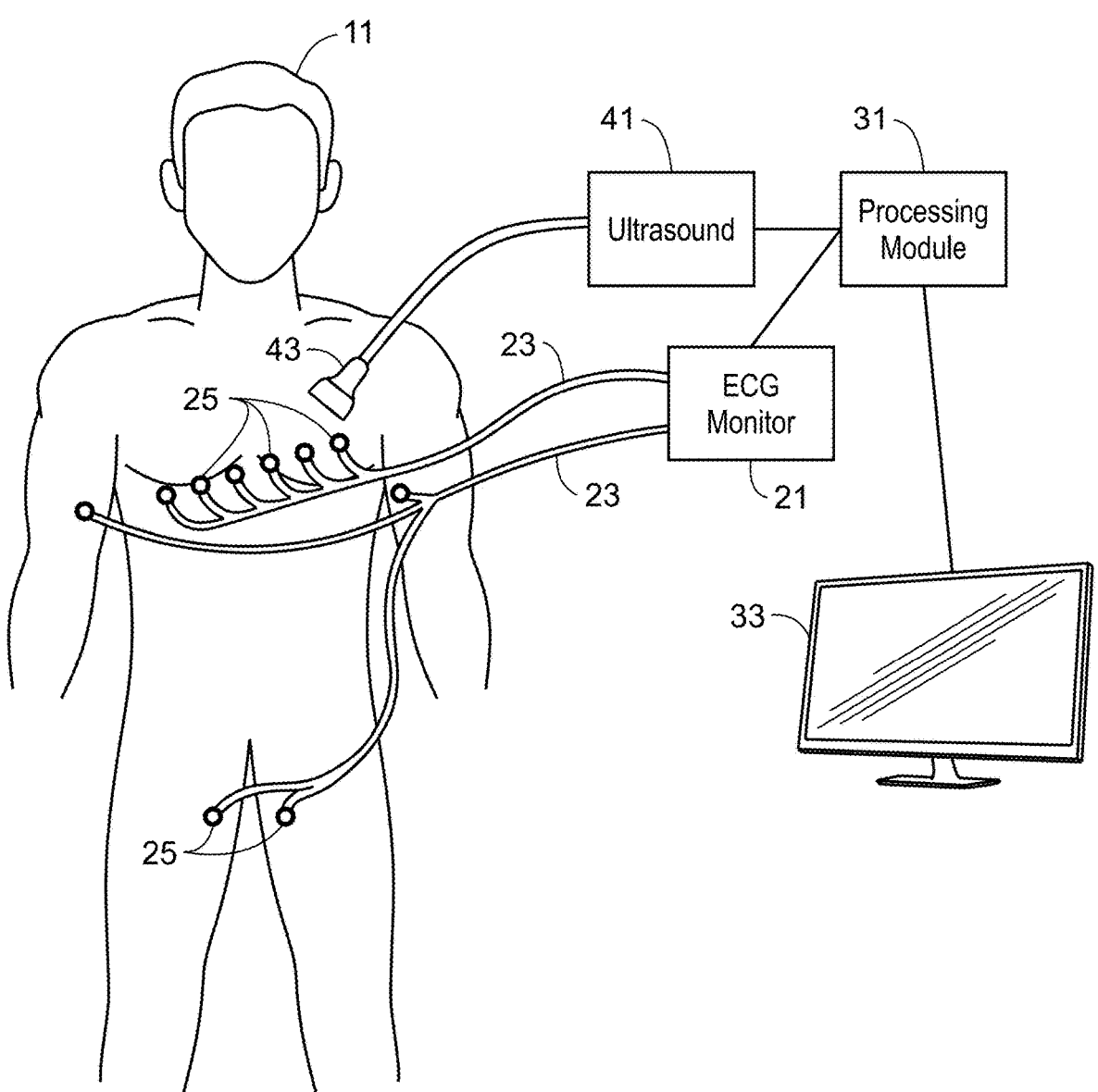
FIG. 6 is a diagram of a system for obtaining electrical and mechanical cardiac information from a patient, generating three-dimensional representations of the information, and displaying the information to a medical professional, according to an embodiment.

FIG. 6 shows a system for obtaining electrical and mechanical cardiac information from a patient, generating three-dimensional representations of the information, and displaying the information to a medical professional, according to an embodiment.

FIG. 6 shows an ECG and an echocardiogram being simultaneously administered to a patient. The echocardiogram may be obtained using an ultrasound device 41 having a probe 43 including one or more transducers. The ECG may be obtained using an ECG monitor 21. The ECG and echocardiogram may be obtained using methods known in the art. The data obtained from the ultrasound device 41 and ECG monitor 21 may be processed by a processing module to obtain 3D rendering of the data for output on a display.

Figure 7A:
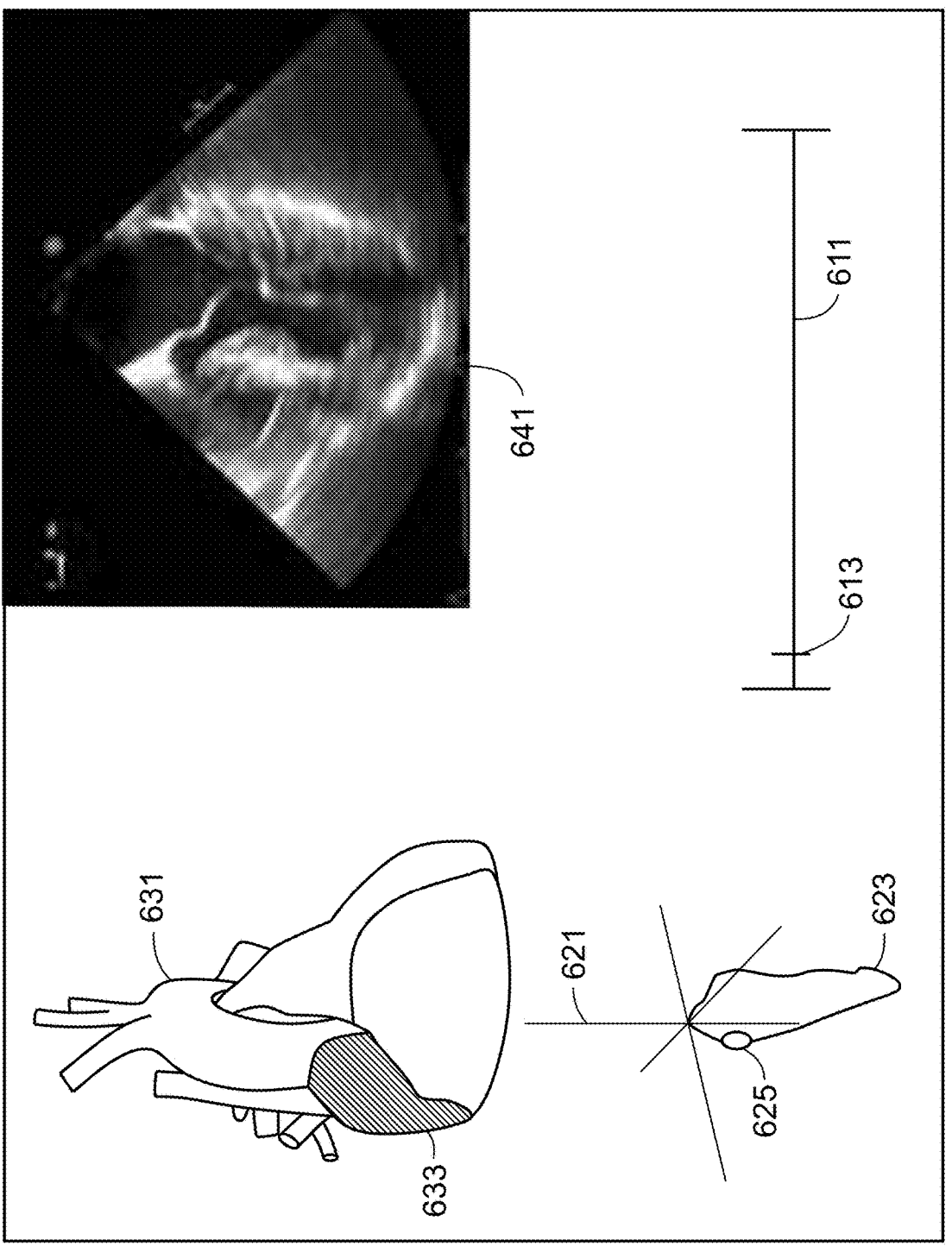
FIGS. 7A-7B show a user interface for comparative analysis of electrical and mechanical cardiac information, according to an embodiment.
Figure 7B:
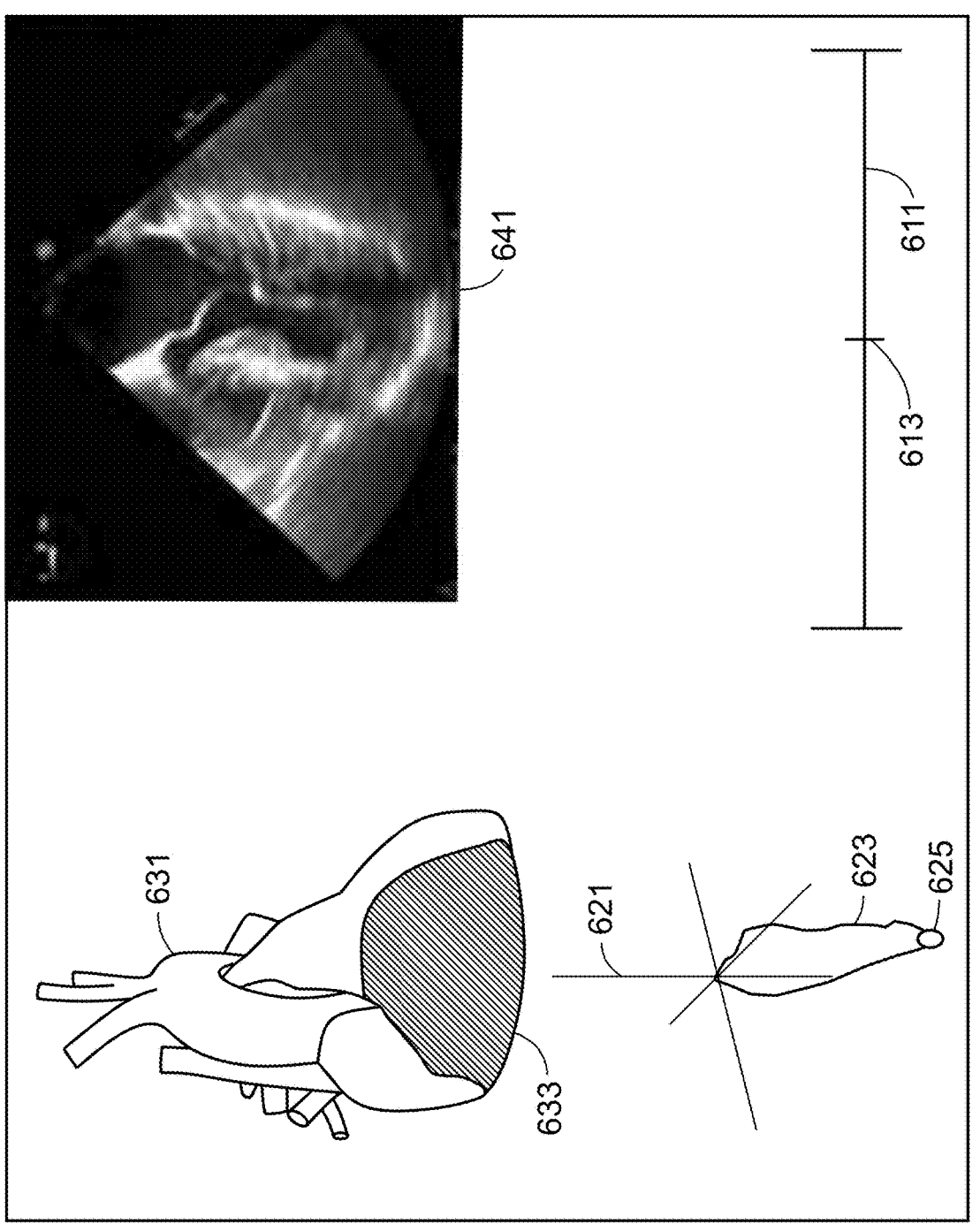

FIGS. 7A-7B show a user interface for comparative analysis of electrical and mechanical cardiac information, according to an embodiment. The electrical and mechanical data may be obtained from a same period of time. That is, an ECG and echocardiogram may be administered at the same time to provide two sets of data from the same time period for comparative analysis.

As shown in FIG. 7A, the user interface may include a time scale 611. The time scale 611 may span a single heart beat or multiple heart beats. As a user may move a sliding time cursor 613 along the time scale 611, each of the renderings in the user interface may be adjusted based on the selected time. According to an embodiment, the time scale 611 may include evenly divided increments, such as portions of a second.

The time cursor 613 is correlated to a point in time in the ECG data and the echocardiogram data. As such, the objects displayed in the user interface may be rendered based on the data corresponding to the time point of the time cursor 613.

As shown in FIG. 7A, the user interface may display an xyz axis 621 which includes a 3D rendering of a cardiac vector loop 623 based on the ECG data. Displaying and controlling the xyz axis 621 and vector loop 623 may be performed in the same manner as discussed above with respect to FIGS. 2A-E and 3A-E. For example, the point of view from which the xyz axis 621 and vector loop 623 is displayed may be changed by dragging a cursor. While the example of FIGS. 7A-7B displays only a single vector loop (QRS loop), other embodiment may display multiple loops, such as the QRS loop and the T loop. According to an embodiment, maximum vectors and angles between the maximum vector may also be displayed in response to a user input.

A loop cursor 625 may be provided on the vector loop 623 to indicate the point in time of the time cursor 613 on the time scale 611. Moving the loop cursor 625 along the vector loop 623 may cause the displayed renderings and time cursor 613 to be adjusted based on the time point associated with the cardiac vector pointing to the loop cursor 625.

The user interface may simultaneously display a 3D rendering of a heart 631 with the vector loop 623. The 3D rendering of the heart 631 may be aligned with the vector loop 623. That is, y-z plane of the displayed axis may be aligned with the coronal plane of the heart, the z-x plane of the axis may be aligned with the transverse plane of the heart, and the y-x plane of the axis may be aligned with the sagittal plane of the heart. According to an embodiment, changing a point of view of either the 3D rending of heart 631 or the vector loop 623 may change a point of view of both of the 3D rending of the heart 631 and vector loop 623. For example, if a point of view of the 3D rending of the heart 631 is changed through dragging a cursor, the vector loop 623 may be changed in a similar manner so the two 3D renderings remain aligned for comparative analysis. According to other embodiments, the vector loop 623 and 3D rending of the heart 631 may be rotated separately.

The echocardiogram data indicates when different portions of the heart are contracting during a heartbeat. As the user slides the time cursor 613 along the time scale 611, the portion of the heart contracting at the time corresponding to the time cursor 613 may be shown on the 3D rendering of the heart 630. As shown in the example of FIGS. 7A-7B, the portion of the heart that is contracting at any given time, based on the echocardiogram data, is highlighted 633. According to other embodiments, the 3D rendering of the heart 631 may be controlled to contract in a similar manner as the patient's heart. For example, when the echocardiogram data shows a portion of the patient's heart contracting a specific amount at a specific time, that same portion of the 3D rendering 631 may contract in the same amount when the time cursor 613 is at that time to emulate that actual heart activity of the patient.

The user interface may also show a two-dimensional (2D) echocardiogram image 641. The 2D image 641 may be generated using known methods in the art. The 2D image 641 may also be adjusted based on the time cursor of the time scale.

As shown in FIG. 7A, the time cursor 613 is at the beginning of the time scale 611. Each of the vector loop cursor 625, the 3D rendering of the heart 631, and the 2D image 641 may be synchronized to represent the heart at the point in time corresponding to the time cursor 613. As shown in FIG. 7A, the loop cursor 625 indicates the time-point on the cardiac vector corresponding the time cursor 613 on the time scale 611. That is, the ECG data from the time corresponding to the time cursor 611 provides a cardiac vector pointing to the loop cursor 625.

In FIG. 7A, the echocardiogram from the time corresponding to the timepoint of the cursor 613 shows the right atrium contracting. As shown in FIG. 7A, on the 3D rendering of the heart 631, the right atrium is highlighted to indicated that the patient's right atrium was contracting at the point in time of the time cursor 613. According to other embodiments, to provide additional insights, the right atrium of the 3D heart may be rendered to display a realistic contraction that would be similar to the patient's actual heart during the echocardiogram. That is, any movement of the heart shown in the echocardiogram may similarly be shown on the 3D rendering of the heart using techniques known in the art.

As also shown in FIG. 7A, the 2D echocardiogram image 641 from the time associated with the timepoint of the cursor 613 is displayed.

As shown in FIG. 7B, the time cursor 613 is in the middle of the timescale 611. As time and the heartbeat progress, the cardiac vector progresses around the vector loop. As seen in FIG. 7B, the loop cursor 625 indicating a current cardiac vector has progressed around the vector loop 623 based on the progression of time along the time scale 611.

As also shown in FIG. 7B, on the 3D rendering of the heart 631, the left and right ventricles are highlighted 633 since these structures of the heart are contracting at the point in time corresponding to the time cursor 613.

As also shown in FIG. 7B, the 2D echocardiogram image 641 from the time associated with the new timepoint of the time cursor 613 is displayed.

The user interface of FIGS. 7A-B may also include a selection menu similar to FIG. 5. The selection men may include icons representing measurements taken at different times. A user may select an icon to see the corresponding cardiac information displayed as shown in FIGS. 7A and 7B.

According to an embodiment, a timepoint may be selected by selecting a location on the vector loop. Selecting a point or sliding along the vector loop may perform the same function as moving the time cursor along the time scale.

According to an embodiment, the 3D rendering of the heart and the vector loop may be provided on a same xyz axis.

Figure 8:
FIG. 8 is a diagram of an electronic device that is a component of the system, according to an implementation.
Figure 8:
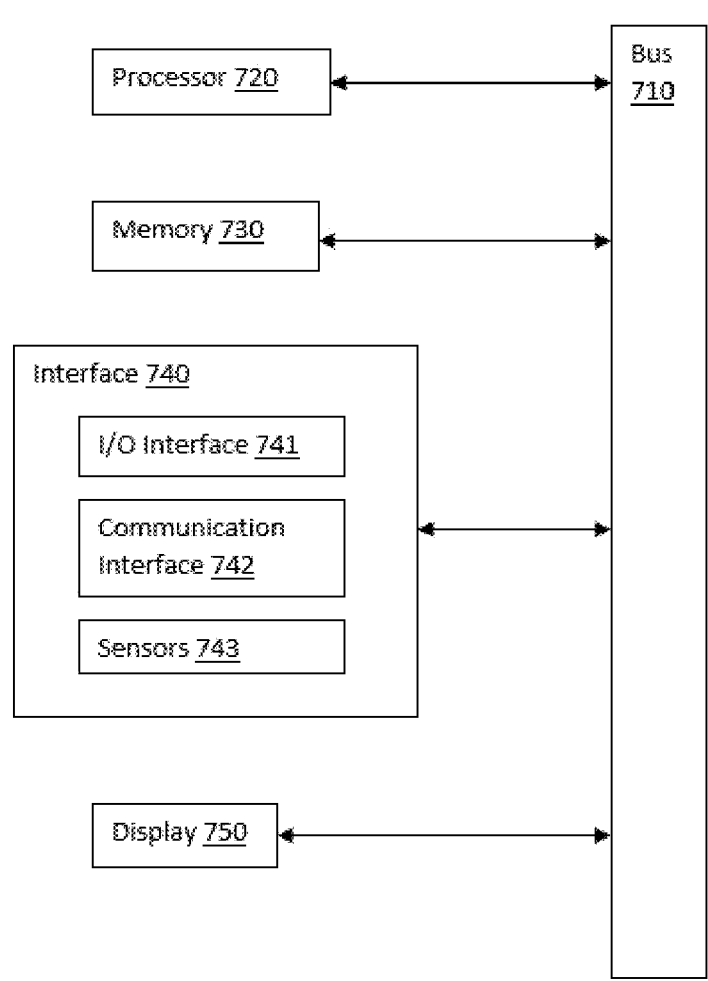
Figure 9:
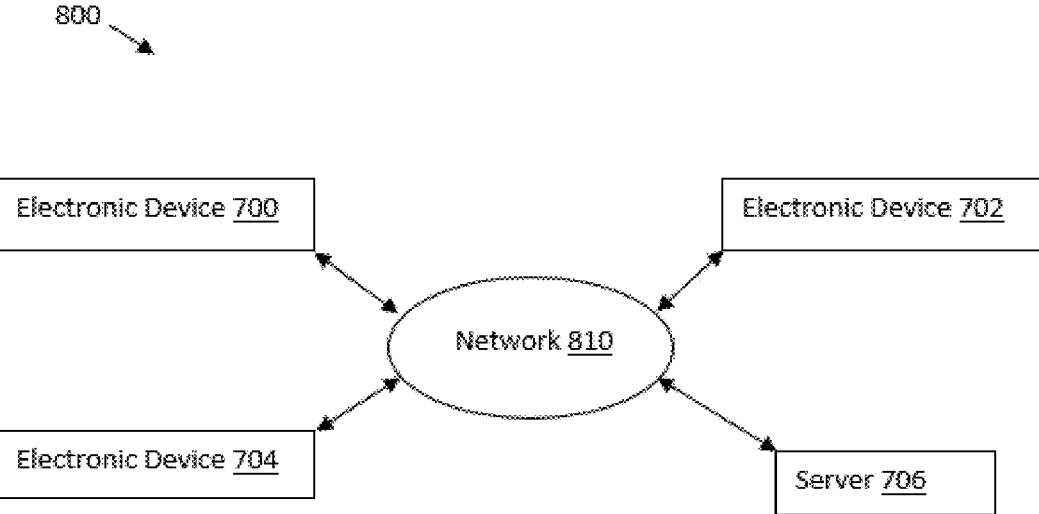
FIG. 9 is a diagram of a network environment on which the system is operated, according to an implementation.

The methods of displaying cardiac information may be deployed, partially deployed, operated, or accessed on electronic device 700 of FIG. 8 in a network environment 800 as shown in FIG. 9, according to an embodiment. FIGS. 8 and 9 are for illustration only, and other embodiments of the electronic device and environment could be used without departing from the scope of this disclosure.

As shown in FIG. 8 electronic device 700 may include at least one of a bus 710, a processor 720 (or a plurality of processors), a memory 730, an interface 740, and a display 750.

Bus 710 may include a circuit for connecting the components 720, 730, 740, and 750 with one another. Bus 710 may function as a communication system for transferring data between the components, or between electronic devices.

Processor 720 may include one or more of a central processing unit (CPU), a graphics processor unit (GPU), an accelerated processing unit (APU), many integrated core (MIC), a field-programmable gate array (FPGA), or a digital signal processing (DSP). Processor 720 may control at least one of other components of electronic device 700, and/or perform an operation or data processing relating to communication. Processor 720 may execute one or more programs stored in memory 630.

Memory 730 may include a volatile and/or a non-volatile memory. Memory 730 may store information, such as one or more commands, data, programs (one or more instructions), or applications, etc., that is related to at least one other component of the electronic device 700 and for driving and controlling electronic device 700. For example, commands or data may formulate an operating system (OS). Information stored in memory 730 may be executed by processor 720.

The application may include one or more embodiments as discussed above. These functions can be performed by a single application or by multiple applications that each carry out one or more of these functions.

Display 750 may include, for example, a liquid crystal display (LCD), a light emitting diode (LED) display, an organic light emitting diode (OLED) display, a quantum-dot light emitting diode (QLED) display, a microelectromechanical systems (MEMS) display, or an electronic paper display. Display 750 can also be a depth-aware display, such as a multi-focal display. Display 750 is able to present, for example, various contents (such as text, images, videos, icons, or symbols).

Interface 740 may include input/output (I/O) interface 741, communication interface 742, and/or one or more sensors 743. I/O interface 741 serves as an interface that can, for example, transfer commands or data between a user or other external devices and other component(s) of electronic device 700. The I/O interface 741 may provide a human-machine user interface which provides information to a user and receives information from the user.

Sensor(s) 743 may meter a physical quantity or detect an activation state of electronic device 700 and may convert metered or detected information into an electrical signal. For example, sensor(s) 743 may include one or more cameras or other imaging sensors for capturing images of scenes. The sensor(s) 743 may also include a microphone, a keyboard, a mouse, a touchscreen, one or more buttons for touch input, a gyroscope or gyro sensor, an air pressure sensor, a magnetic sensor or magnetometer, an acceleration sensor or accelerometer, a grip sensor, a proximity sensor, a color sensor (such as a red green blue (RGB) sensor), a biophysical sensor, a temperature sensor, a humidity sensor, an illumination sensor, an ultraviolet (UV) sensor, an electromyography (EMG) sensor, an electroencephalogram (EEG) sensor, an electrocardiogram (EGG) sensor, an infrared (IR) sensor, an ultrasound sensor, an iris sensor, or a fingerprint sensor. The sensor(s) 743 can further include an inertial measurement unit. In addition, sensor(s) 743 can include a control circuit for controlling at least one of the sensors included here. Any of these sensor(s) 743 can be located within or coupled to electronic device 700. Sensor(s) 743 may be used to detect touch input, gesture input, hovering input using an electronic pen or a body portion of a user, etc.

Communication interface 742, for example, may be able to set up communication between electronic device 700 and an external electronic device (such as a first electronic device 702, a second electronic device 704, or a server 706 as shown in FIG. 9). As shown in FIG. 9, communication interface 742 may be connected with a network 710 through wireless or wired communication architecture to communicate with an external electronic device. Communication interface 742 may be a wired or wireless transceiver or any other component for transmitting and receiving signals.

FIG. 9 shows an example network configuration 800 according to an embodiment. Electronic device 700 of FIG. 8 may be connected with a first external electronic device 702, a second external electronic device 704, or a server 706 through network 810. Electronic device 700 may be wearable device, an electronic device-mountable wearable device (such as an FIMD), etc. When electronic device 700 is mounted in the electronic device 702 (such as the FIMD), electronic device 700 may communicate with electronic device 702 through communication interface 742. Electronic device 700 may be directly connected with electronic device 702 to communicate with electronic device 702 without involving a separate network. Electronic device 700 may also be an augmented reality wearable device, such as eyeglasses, that include one or more cameras.

The first and second external electronic devices 702 and 704 and server 506 may each be a device of a same or a different type than electronic device 700. According to some embodiments, server 706 may include a group of one or more servers. Also, according to some embodiments, all or some of the operations executed on electronic device 700 may be executed on another or multiple other electronic devices (such as electronic devices 702 and 704 or server 706). Further, according to some embodiments, when electronic device 700 should perform some function or service automatically or at a request, electronic device 700, instead of executing the function or service on its own or additionally, can request another device (such as electronic devices 702 and 704 or server 706) to perform at least some functions associated therewith. The other electronic device (such as electronic devices 602 and 704 or server 706) may be able to execute the requested functions or additional functions and transfer a result of the execution to electronic device 700. Electronic device 700 can provide a requested function or service by processing the received result as it is or additionally. To that end, a cloud computing, distributed computing, or client-server computing technique may be used, for example. While FIGS. 8 and 9 show that electronic device 700 including communication interface 742 to communicate with external electronic devices 702 and 704 or server 706 via the network 810, electronic device 700 may be independently operated without a separate communication function according to some embodiments.

Server 706 may include the same or similar components 710, 720, 730, 740, and 750 as electronic device 700 (or a suitable subset thereof). Server 706 may support driving electronic device 700 by performing at least one of operations (or functions) implemented on electronic device 700. For example, server 706 can include a processing module or processor that may support processor 720 of electronic device 700.

The wireless communication may be able to use at least one of, for example, long term evolution (LTE), long term evolution-advanced (LTE-A), 5th generation wireless system (5G), millimeter-wave or 60 GFIz wireless communication, Wireless USB, code division multiple access (CDMA), wideband code division multiple access (WCDMA), universal mobile telecommunication system (UMTS), wireless broadband (WiBro), or global system for mobile communication (GSM), as a cellular communication protocol. The wired connection may include, for example, at least one of a universal serial bus (USB), high definition multimedia interface (HDMI), recommended standard 232 (RS-232), or plain old telephone service (POTS). The network 810 includes at least one communication network, such as a computer network (like a local area network (LAN) or wide area network (WAN)), Internet, or a telephone network.

Although FIG. 9 shows one example of a network configuration 800 including an electronic device 700, two external electronic devices 702 and 704, and a server 706, various changes may be made to FIG. 9. For example, the network configuration 800 could include any number of each component in any suitable arrangement. In general, computing and communication systems come in a wide variety of configurations, and FIG. 9 does not limit the scope of this disclosure to any particular configuration. Also, while FIG. 9 shows one operational environment in which various features disclosed in this patent document can be used, these features could be used in any other suitable system.

The event detection method may be written as computer-executable programs or instructions that may be stored in a medium.

The medium may continuously store the computer-executable programs or instructions, or temporarily store the computer-executable programs or instructions for execution or downloading. Also, the medium may be any one of various recording media or storage media in which a single piece or plurality of pieces of hardware are combined, and the medium is not limited to a medium directly connected to electronic device 700, but may be distributed on a network. Examples of the medium include magnetic media, such as a hard disk, a floppy disk, and a magnetic tape, optical recording media, such as CD-ROM and DVD, magneto-optical media such as a floptical disk, and ROM, RAM, and a flash memory, which are configured to store program instructions. Other examples of the medium include recording media and storage media managed by application stores distributing applications or by websites, servers, and the like supplying or distributing other various types of software.

The method of displaying cardiac information may be provided in a form of downloadable software. A computer program product may include a product (for example, a downloadable application) in a form of a software program electronically distributed through a manufacturer or an electronic market. For electronic distribution, at least a part of the software program may be stored in a storage medium or may be temporarily generated. In this case, the storage medium may be a server or a storage medium of server 706.

Figure 10:
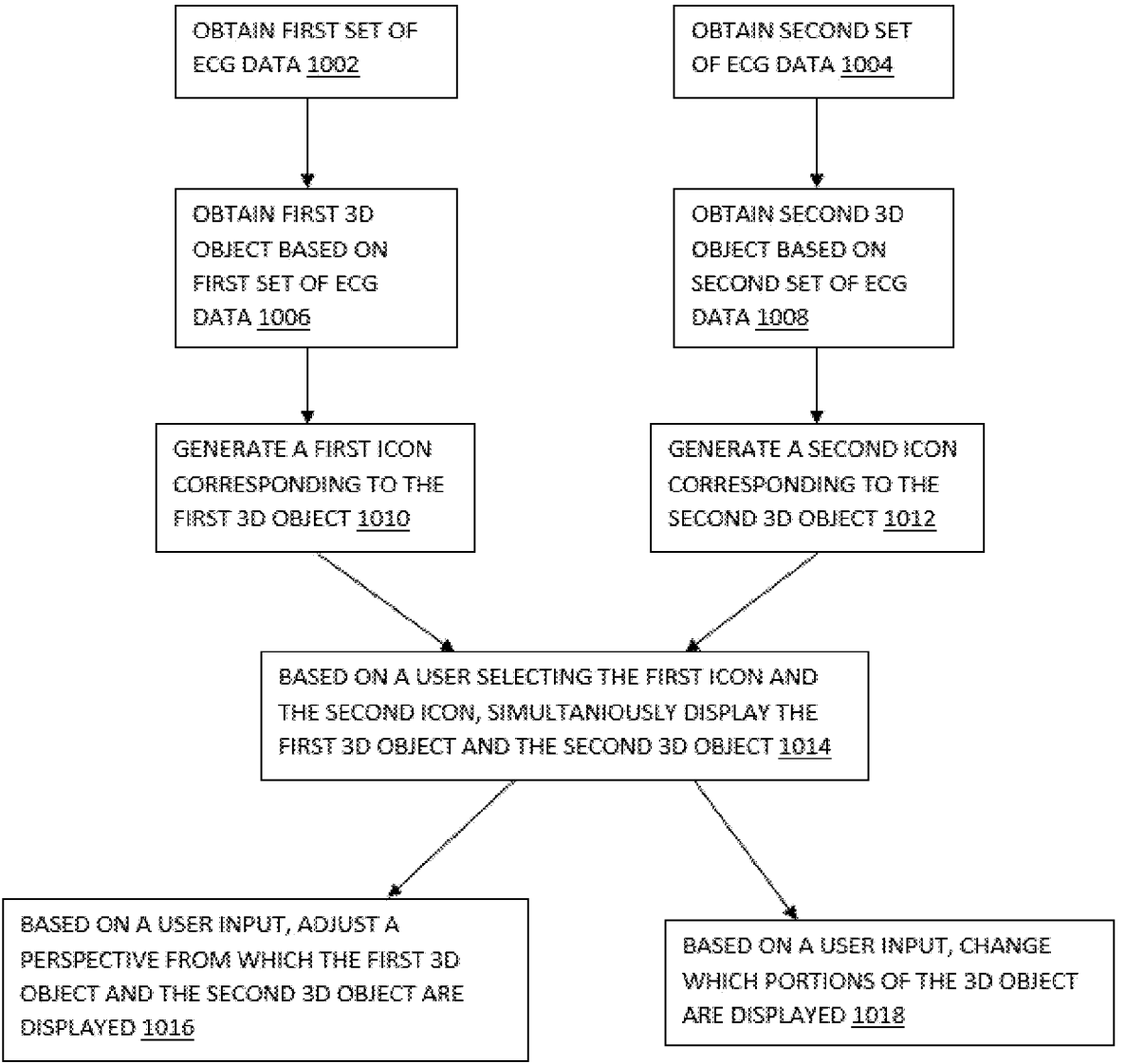
FIG. 10 is a flowchart of a method of displaying cardiac information for comparative analysis, according to an embodiment.

FIG. 10 is a flowchart of a method of displaying cardiac information for comparative analysis, according to an embodiment. The method may be implemented on electronic device 700, in network environment 800, and/or in the environment of FIG. 1.

At operation 1002, a first set of ECG data may be obtained and at operation 1004 a second set of ECG data may be obtained. The ECG data may be obtained using an ECG monitor, such as a 6 lead or a 12 lead ECG monitor. The ECG data may be processes, such as through filtering by the ECG monitor or a processor of another device. According to an embodiment, the ECG data may be obtained over a network and/or from a database storing multiple sets of ECG data. The first set of ECG data may be from an ECG administered during a first timer period and the second set of ECG data may be obtained from an ECG administered during a second time period removed from the first time period (e.g. ECGs are administered 1 month apart).

At operation 1006, a first 3D object is obtained based on the first set of ECG data and at operation 1008, a second 3D object is obtained based on the second set of ECG data. The 3D objects may be obtained from a computer processor that generates the object based on the ECG data. According to some aspects, the 3D object may be obtained over a network, such as from a database or another device.

Each 3D object may include one or more of a cardiac vector loop and vectors making up the vector loop, such as a maximum vector of the vector loop. According to an aspect, the first 3D object may be a vector loop and the second 3D object may be a vector loop. According to another aspect, the first 3D object may be a maximum vector of a vector loop and the second 3D object may be a maximum vector of a vector loop. According to yet another aspect, the first 3D object may include one or more vector loops and/or one or more maximum vectors and the second 3D object may include one or more vector loops and one or more maximum vectors.

The cardiac vector loops may include one or more of a QRS loop, a T loop, and a P loop. The maximum vectors may include one or more of a maximum vector of the QRS loop, a maximum vector of the T loop, and a maximum vector of the P loop.

At operation 1010, a first icon may be generated for the first 3D object and at operation 1012 a second icon may be generated for the second 3D object. The icons may be displayed on a user interface for selection by a user. The icons may include information corresponding to the 3D object, such as a time at which the measurement was administered, an initial rating of the results (e.g. normal, abnormal), a device by which the measurement was performed, etc.

For example, as shown in the non-limiting example of FIG. 5, the icons include a time at which the ECG was administered, a rating, and a relative age indicator. The icons may be organized based on a user selection. As shown in FIG. 5, the user has selected serial presentation which organizes the icons based on chronological order of the time at which the ECGs were administered. Other known organization rules may be used, such as based on the rating or the measuring device.

At operation 1014, based on a user selecting the first icon and the second icon, the first 3D object and the second 3D object may be simultaneously displayed.

For example, a user may select the first icon. In response to the first icon being selected, the first 3D object may be displayed on an xyz axis. The user may then select the second icon. In response to the second icon being selected, the second 3D object may be displayed on the xyz axis along with the first 3D object. The user may then deselect the first icon. Responsive to the user deselecting the first icon, the first 3D object may be removed from the xyz axis.

According to an aspect, the first 3D object and the second 3D object may be aligned for comparative analysis. For example, the 3D objects may be aligned relative to the xyz axis and/or relative to each other. The 3D objects may be initially displayed from a preset point of view, such a perspective view. According to an aspect, the object may be displayed from a point of view which shows the largest difference between the objects. For example, if a difference between the 3D objects is only shown when displayed from an overhead z-axis point of view, the object may be initially displayed from this point of view so the differences are immediately presented to a medical professional.

At operation 1016, based on a user input, a perspective from which the 3D objects are display may be adjusted. As discussed with respect to FIGS. 2A-E and 3A-E, the user may change a point of view from which the 3D objects are displayed. The user may also change a view zoom.

For example, a user may click and drag a mouse to rotate the 3D objects. The user may also zoom in or out on the object using a scroller on the mouse.

At operation 1018, based on a user input, different portions of the 3D object may be displayed. A user may select an icon for displaying vector loops of the 3D object and an icon for displaying maximum vectors of the 3D objects. A user may also select one of the 3D objects to cause the other 3D object to disappear so the selected object can be examined more closely.

According to an aspect, a vector gradient may be shown on one or more of the vector loops. The vector gradient may be obtained by calculating a derivative of the vector loop. The loop may then be shaded based on the derivative to show the gradient. The vector gradient may be displayed on a loop in response to a user input, such as selection of an icon.

The vector gradients on cardiac vector loops provide information about the spatial and temporal changes in the electrical activity of the heart. The gradient of the vector loop represents the rate of change of the electrical potential, and this information can be used to diagnose various cardiac conditions. For example, changes in the gradient of the vector loop can indicate changes in the heart's electrical conduction system, which can be associated with heart conditions such as arrhythmias or heart blocks. Additionally, changes in the gradient of the vector loop can be used to evaluate the effectiveness of therapeutic interventions, such as the administration of medications, for example. By analyzing the gradient of the vector loop, medical professionals can gain a deeper understanding of the electrical activity of the heart, which can aid in the diagnosis and management of cardiac conditions.

Figure 11:
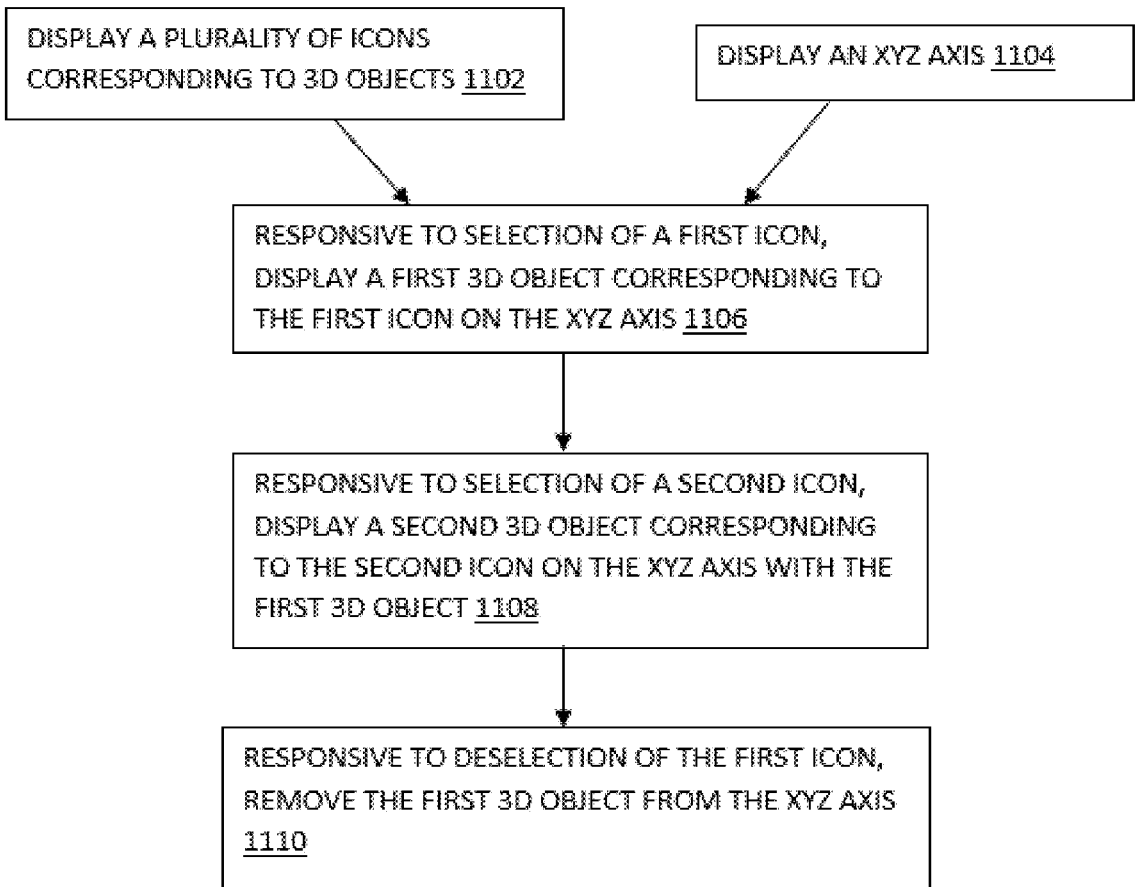
FIG. 11 is a flowchart of a method of displaying cardiac information for comparative analysis, according to an embodiment.

FIG. 11 is a flowchart of a method of displaying cardiac information for comparative analysis, according to an embodiment. The method may be implemented on electronic device 700, in network environment 800, and/or in the environment of FIG. 1.

At operation 1102, a plurality of icons corresponding to 3D objects may be displayed on a user interface. Each object may correspond to an ECG administered at a different time. For example, a first 3D object may be based on an ECG administered on Mar. 1, 2022 and a second 3D object may be based on an ECG administered on Mar. 1, 2023. The 3D object may include cardiac vectors, cardiac vector loops, maximum cardiac vectors, and angles between cardiac vectors. Each icon may display a date (e.g. when the ECG was administered) and a rating (e.g. normal, abnormal). The icons may be sorted based on a user's selection. For example, as shown in FIG. 5, the icons may be displayed serially.

At operation 1104, an xyz axis may be displayed. The icons and the xyz axis may be simultaneously displayed on the user interface.

At operation 1106, in response to the user selecting a first icon via the user interface, the first 3D object corresponding to the first icon may be displayed on the xyz axis. For example, in response to a user selecting the first icon, vector loops based on a ECG administered on Jun. 14, 2017 at 15:34:13 may be displayed on the xyz axis.

At operation 1108, in response to the user selecting a second icon via the user interface, the second 3D object corresponding to the second icon may be displayed on the xyz axis along with the first 3D object, as shown in the non-limited example of FIG. 5. Each of the 3D object may be displayed with distinguishing characteristics, such as color or line type.

At operation 1110, in response to the user deselecting the first icon via the user interface, the first 3D object may be removed from the xyz axis leaving only the second object on the xyz axis.

Figure 12:
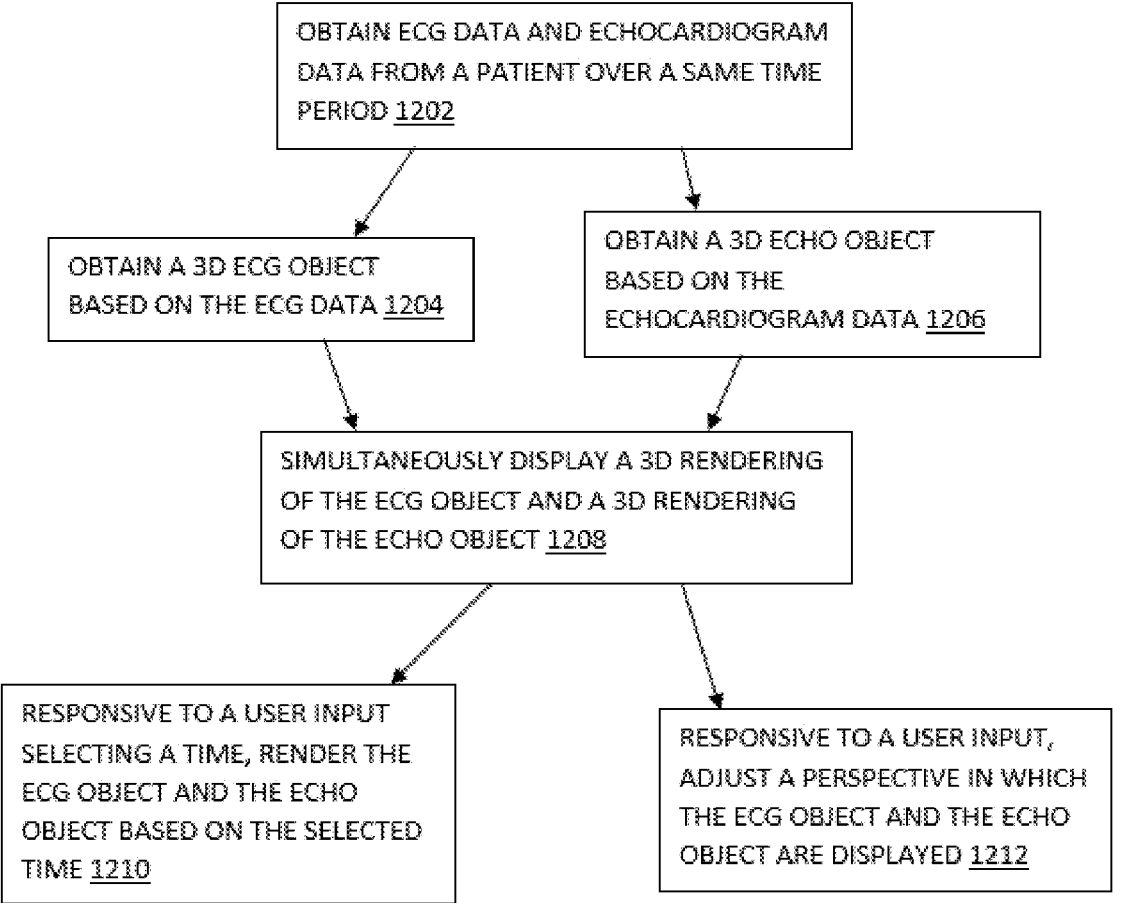
FIG. 12 is a flowchart of a method of displaying cardiac information for comparative analysis, according to an embodiment.

FIG. 12 is a flowchart of a method of displaying cardiac information for comparative analysis, according to an embodiment. The method may be implemented on electronic device 700, in network environment 800, and/or in the environment of FIG. 6.

At operation 1202, ECG data and echocardiogram data may be obtained from a patient over a same time period. As shown in FIG. 6, an ECG and echocardiogram may be simultaneously administered to a patient to obtain two sets of data correspond to a same time period.

At operation 1204, a 3D object based on the ECG data ("ECG object") may be obtained. For example, cardiac vectors, vector loops, and maximum vectors may be generated by a processor based on the ECG data using methods known in the art.

At operation 1206, a 3D object based on the echocardiogram data ("ECHO object") may be obtained. For example, a 3D rendering of a heart that mimics the movement of the patient's heart, as shown by the echocardiogram data, may be generated by a processor using known method in the art.

At operation 1208, a 3D rendering of the ECG object and a 3D rendering of the ECHO object may be simultaneously displayed on a user interface. As shown in the non-limiting examples of FIGS. 7A-7B, the ECG object and the ECHO object may be simultaneously displayed next to each other for comparative analysis.

At operation 1210, in response to a user input selecting a time, the ECG object and the ECHO object may be rendered based on the selected time. For example, when the ECG object is a cardiac vector loop, a loop cursor may be provided on the loop to indicate a cardiac vector corresponding to a point in time. As such, the loop cursor may be rendered at different positions on the loop at different times based on the ECG data. The ECHO object may include a 3D rending of a heart. Throughout a cardiac cycle, the echocardiogram data tracks which portions of the heart are contracting or moving. When a time is selected by a user, the ECHO object may be rendered to indicate which portion of the heart is contracting at that time based on the echocardiogram data.

For example, a user may move a time cursor along a time scale displayed on a user interface. The ECG object may be rendered based on ECG data corresponding to the time of the time cursor and the ECHO object may be rendered based on echocardiogram data corresponding to the time of the time cursor.

At operation 1212, in response to a user input, a perspective from which the 3D objects are display may be adjusted. As discussed with respect to FIGS. 2A-E and 3A-E, the user may change a point of view from which the 3D objects are displayed. The user may also change a view zoom.

For example, a user may click and drag a mouse to rotate the 3D objects. The user may also zoom in or out on the object using a scroller on the mouse.

The perspective on both the ECG object and the ECHO object may remain the same. That is, an input for rotating may rotate both objects the same amount.

Figure 13:
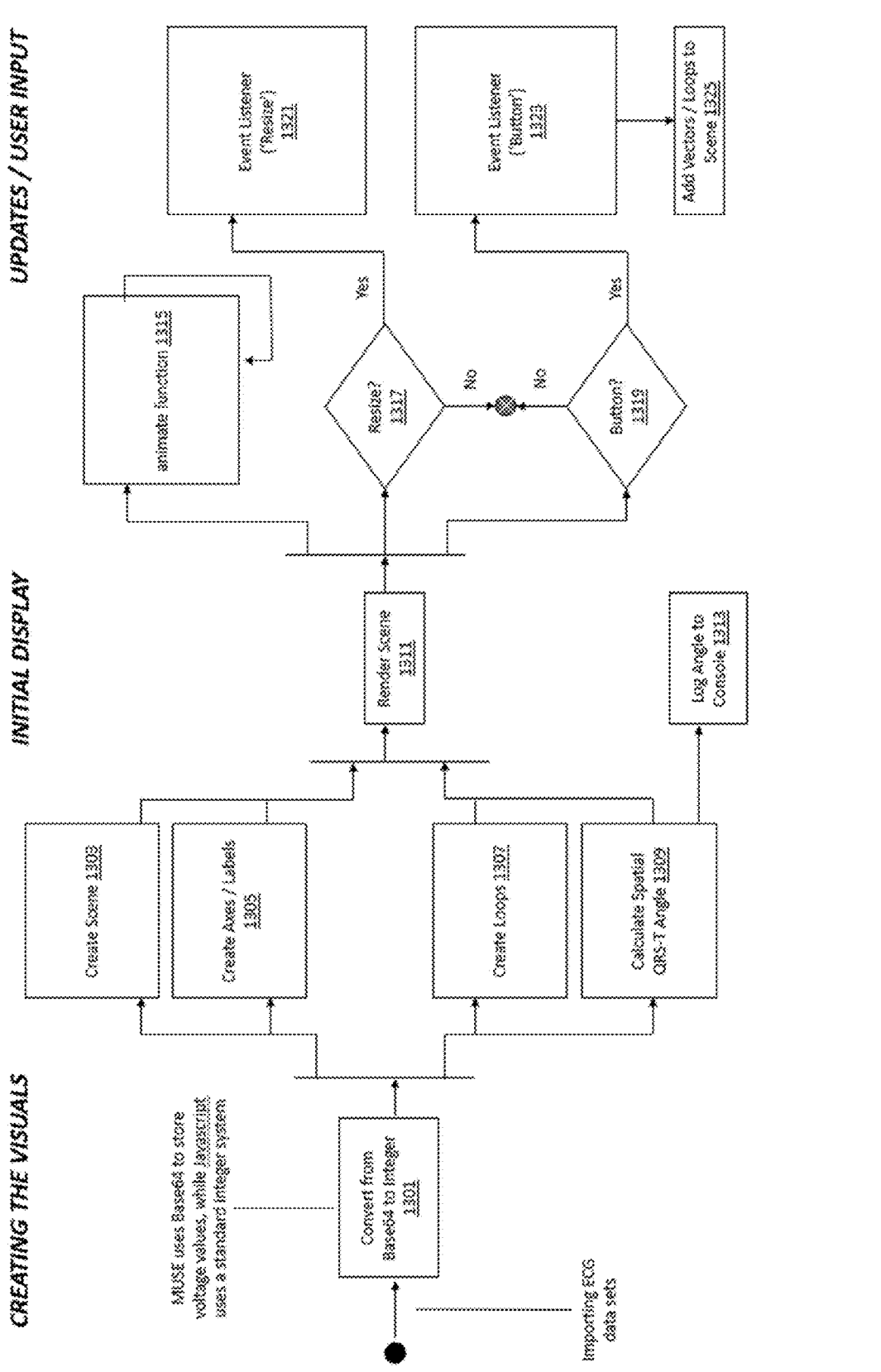
FIG. 13 is a flowchart of a process of displaying three-dimensional cardiac information, according to an embodiment.

FIG. 13 is a flowchart of a process of displaying three-dimensional cardiac information, according to an embodiment.

At operation 1301, imported ECG data may be converted from Base64 to integer. ECG monitoring device may provide the data in Base64 so the data may be converted to integer for use with specific programing languages, such as Javascript.

At operation 1303, a scene in which the cardiac information will be displayed may be created. At operation 1305, an axis and labels for the scene are created. For example, a labeled xyz axis may be created.

At operation 1307, 3D cardiac vector loops may be created based on the ECG data. The 3D cardiac vector loops may be obtained using methods known in the art. At operation 1309, a spatial QRS-T angle may be calculated based on the ECG data. The spatial QRS-T angle may be obtaining using methods known in the art.

At operation 1311, the 3D cardiac vector loops and the xyz axis may be rendered in the scene. For example, the 3D cardiac vector loops may be rendered on the xyz axis. The spatial QRS-T angle may also be rendered in the scene.

At operation 1313, the QRS-T angle may be logged to a consol.

If resizing the 3D objects is desired at operation 1317, a user input is detected at 1321. If vectors or loops are desired to be added to the scene, a button selection is detected at operation 1323 and vectors or loops may be added to the scene at operation 1325 based on the button selection.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

According to an implementation, a system for comparative analysis of cardiac information may include: an electrocardiogram (ECG) device comprising a plurality of electrodes and a monitor configured to measure electrical signals through the electrodes, the ECG device being configured to provide ECG data; a user interface configured to provide information to a user and obtain information from a user; a memory storing instructions; and a processor configured to execute the instructions to: obtain a first set of ECG data from the ECG device, the first set of ECG data being measured from a patient during a first time period; obtain a second set of ECG data from the ECG device, the second set of ECG data being measured from the patient during a second time period distinct from the first time period; obtain a first three-dimensional (3D) object based on the first set of ECG data; obtain a second 3D object based on the second set of ECG data; and control the user interface to simultaneously display the first 3D object and the second 3D object on a same axis.

According to an implementation, the first 3D object may include a vector loop and the second 3D object is a vector loop.

According to an implementation, the first 3D object may include a spatial QRS-T angle and the second 3D object is a spatial QRS-T angle.

According to an implementation, the first 3D object may include one or more of a QRS vector loop, a vector corresponding to a maximum of the QRS vector loop, a T vector loop, a vector corresponding to a maximum of the T vector loop, and a Q-RST angle between the vector corresponding to the maximum of the QRS vector loop and the vector corresponding to the maximum of the T vector loop, and the second 3D object may include one or more of a QRS vector loop, a vector corresponding to a maximum of the QRS vector loop, a T vector loop, a vector corresponding to a maximum of the T vector loop, and a Q-RST angle between the vector corresponding to the maximum of the QRS vector loop and the vector corresponding to the maximum of the T vector loop.

The processor may be further configured to execute the instructions to: control the user interface to display two or more of an icon for viewing vector loops, an icon for viewing maximum vectors, and an icon for viewing QRS-T angle; responsive to the user selecting the icon for viewing vector loops, control the user interface to display the QRS vector loop and T vector loop of the first 3D object and the second 3D object; responsive to the user selecting the icon for viewing maximum vectors, control the user interface to display the maximum vectors of the first 3D object and the maximum vectors of the second 3D object, and responsive to the user selecting the icon for viewing QRS-T angle, control the user interface to display the QRS-T angle for the first 3D object and the QRS-T angle for the second 3D object.

According to an implementation, the icon outputs may be simultaneously displayed when multiple icons are selected.

According to an implementation, the processor may be further configured to execute the instructions to: responsive to selecting a displayed QRS-T angle of the first 3D object, control the user interface to display a size of the QRS-T angle of the first 3D object in text; and responsive to selecting a displayed QRS-T angle of the second 3D object, control the user interface to display a size of the QRS-T angle of the second 3D object in text.

According to an implementation, the processor may be further configured to execute the instructions to determine a point of view showing a largest difference between the first 3D object and the second 3D object. Simultaneously displaying the first 3D object and the second 3D object may include initially displaying the first 3D object and the second 3D object from the point of view.

According to an implementation, the processor may be further configured to execute the instructions to aligning one of a QRS axis, T axis, and P axis of the displayed first 3D object and the displayed second 3D object.

According to an implementation, the processor may be further configured to execute the instructions to: calculate a derivative of the vector loop of the first 3D object; and shade the vector loop of the first 3D object based on the calculated integral to show the vector gradient.

According to an implementation, the processor may be further configured to execute the instructions to, responsive to a user input, change a point of view from which the first 3D object and the second 3D object are displayed.

According to an implementation, a system for comparative analysis of cardiac information may include a user interface configured to provide information to a user and obtain information from a user; a memory storing instructions; and a processor configured to execute the instructions to: control the user interface to display a plurality of icons corresponding to three-dimensional (3D) objects, each 3D object being obtained from a different set of ECG data, each set of ECG data being obtained during a distinct time period; control the user interface to display an xyz axis simultaneously with the plurality of icons; and responsive to selection of an icon, control the user interface to display a 3D object corresponding to the icon on the xyz axis. Multiple 3D objects may be simultaneously displayed on the xyz axis in response to multiple icons being selected.

According to an implementation, the processor may be further configured to execute the instructions to, responsive to deselection of an icon, control the user interface to remove a 3D object corresponding to the deselected icon from the xyz axis.

According to an implementation, each icon may indicate a time at which a corresponding ECG measurement was taken.

According to an implementation, the icons may be ordered sequentially based on a time at which a corresponding ECG measurements were taken.

According to an implementation, each 3D object may be displayed in a distinctive color different from the other 3D objects.

According to an implementation, a method of displaying cardiac information, may include obtaining a first set of ECG data, the first set of ECG data being measured from a patient during a first time period; obtaining a second set of ECG data, the second set of ECG data being measured from the patient during a second time period distinct from the first time period; obtaining a first three-dimensional (3D) object based on the first set of ECG data; obtaining a second 3D object based on the second set of ECG data; and simultaneously displaying the first 3D object and the second 3D object on a same axis.

According to an implementation, the first 3D object may include one or more of a vector loop spatial QRS-T angle and the second 3D object comprises one or more of a vector loop spatial QRS-T angle.

According to an implementation, the first 3D object may include one or more of a QRS vector loop, a vector corresponding to a maximum of the QRS vector loop, a T vector loop, a vector corresponding to a maximum of the T vector loop, and a Q-RST angle between the vector corresponding to the maximum of the QRS vector loop and the vector corresponding to the maximum of the T vector loop, and the second 3D object may include one or more of a QRS vector loop, a vector corresponding to a maximum of the QRS vector loop, a T vector loop, a vector corresponding to a maximum of the T vector loop, and a Q-RST angle between the vector corresponding to the maximum of the QRS vector loop and the vector corresponding to the maximum of the T vector loop.

According to an implementation, the method may further include providing two or more of an icon for viewing vector loops, an icon for viewing maximum vectors, and an icon for viewing QRS-T angle; responsive to the user selecting the icon for viewing vector loops, displaying the QRS vector loop and T vector loop of the first 3D object and the second 3D object responsive to the user selecting the icon for viewing maximum vectors, displaying the maximum vectors of the first 3D object and the maximum vectors of the second 3D object, and responsive to the user selecting the icon for viewing QRS-T angle, displaying the QRS-T angle for the first 3D object and the QRS-T angle for the second 3D object.

According to an implementation, the method may further include obtaining a max QRS vector and a max T wave vector from the ECG data; obtaining an integral of the max QRS vector and the max T-wave vector; obtaining a ventricular gradient vector by summing of the integral of the max QRS vector and the integral of the max T vector; and displaying the ventricular gradient vector.

According to an implementation, the first set of ECG data may be obtained from a measurement performed by from a first device and the second set of ECG data may be obtained from a measurement performed by a second device.

According to an implementation, a system for comparative analysis of cardiac information may include an electrocardiogram (ECG) device comprising a plurality of electrodes and a monitor configured to measure electrical signals through the electrodes, the ECG device being configured to provide ECG data; an ultrasound device comprising a transducer probe configured to emit and receive sound waves to administer an echocardiogram, the ultrasound device being configured to provide ECHO data; a user interface configured to provide information to a user and obtain information from a user; a memory storing instructions; and a processor configured to execute the instructions to: obtain ECG data and ECHO data from a patient over a same time period, the ECG data being obtained from the ECG device and the ECHO data being obtained from the ultrasound device; obtain an ECG object based on the ECG data, the ECG object being three-dimensional; obtain an ECHO object based on the echocardiogram data, the ECHO object being three-dimensional; and control the user interface to simultaneously display a 3D rendering of the ECG object and a 3D rendering of the ECHO object.

According to an implementation, the processor may be further configured to execute the instructions to: display changes in the 3D rendering of ECG object based on changes in the ECG data over time; and display changes in the 3D rendering of the ECHO object based on changes in the echocardiogram data over time.

According to an implementation, the ECHO object may include an image of heart, and the displaying changes in the 3D rendering of the ECHO object over time includes contracting different portions of the heart based on the echocardiogram data.

According to an implementation, the ECG object may include a vector loop, and the displaying changes in the 3D rendering of the ECG object over time includes showing a time progression of the vector loop based on the ECG data.

According to an implementation, the processor may be further configured to execute the instructions to control both the changes in the ECG object over time and the changes in the ECHO object over time based on a user input.

According to an implementation, the user input may include moving a cursor along a time scale.

According to an implementation, the changes in the 3D rendering of ECG object and the changes in the 3D rendering of the ECHO object may be synchronized based on a shared time scale over the period of time.

According to an implementation, the 3D rendering of the ECG object may be overlayed on the 3D rendering of the ECHO object.

According to an implementation, the 3D rendering of the ECG object may be displayed next to and aligned with the 3D rendering of the ECHO object.

According to an implementation, at least one dimension of the 3D rendering of the ECG object and one dimensional of the 3D rendering of the ECHO object may share a common axis.

According to an implementation, the 3D rendering of the ECG object and the 3D rendering of the ECHO object are displayed in a same window.

According to an implementation, the processor may be further configured to execute the instructions to: obtain a 2D ultrasound image from the echocardiogram data; and control the user interface to simultaneously display the 2D ultrasound image with the 3D rendering of the ECG object and a 3D rendering of the ECHO object.

According to an implementation, a system for comparative analysis of cardiac information may include a memory storing instructions; and a processor configured to execute the instructions to: obtain ECG data and ECHO data from a patient over a same time period, the ECG data being obtained from the ECG device and the ECHO data being obtained from the ultrasound device; obtain an ECG object based on the ECG data, the ECG object being three-dimensional; obtain an ECHO object based on the echocardiogram data, the ECHO object being three-dimensional; and control a display to simultaneously display a 3D rendering of the ECG object and a 3D rendering of the ECHO object.

According to an implementation, the processor may be further configured to execute the instructions to: display changes in the 3D rendering of ECG object based on changes in the ECG data over time; and display changes in the 3D rendering of the ECHO object based on changes in the echocardiogram data over time.

According to an implementation, the ECHO object may include an image of heart, and the displaying changes in the 3D rendering of the ECHO object over time may include contracting different portions of the heart based on the echocardiogram data.

According to an implementation, the ECG object may include a vector loop, and the displaying changes in the 3D rendering of the ECG object over time may include showing a time progression of the vector loop based on the ECG data.

According to an implementation, the processor may be further configured to execute the instructions to control both the changes in the ECG object over time and the changes in the ECHO object over time based on a user input.

According to an implementation, user input may include moving a cursor along a time scale.

According to an implementation, the changes in the 3D rendering of ECG object and the changes in the 3D rendering of the ECHO object may be synchronized based on a shared time scale over the period of time.

According to an implementation, a method of displaying cardiac information, may include obtaining ECG data and echocardiogram data from a patient over a same time period; obtaining an ECG object based on the ECG data, the ECG object being three-dimensional; obtaining an ECHO object based on the echocardiogram data, the ECHO object being three-dimensional; and simultaneously displaying a 3D rendering of the ECG object and a 3D rendering of the ECHO object.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims

The invention claimed is:

1. A system for comparative analysis of cardiac information, the system comprising:
an electrocardiogram (ECG) device comprising a plurality of electrodes and a monitor configured to measure electrical signals through the electrodes, the ECG device being configured to provide ECG data;

a user interface configured to provide information to a user and obtain information from a user;
a memory storing instructions; and
a processor configured to execute the instructions to:
obtain a first set of ECG data from the ECG device, the first set of ECG data being measured from a patient during a first time period;
obtain a second set of ECG data from the ECG device, the second set of ECG data being measured from the patient during a second time period distinct from the first time period;
obtain a first three-dimensional (3D) object based on the first set of ECG data;
obtain a second 3D object based on the second set of ECG data;
shift the second 3D object to align with the first 3D object by aligning a cardiac vector parameter of the second 3D object with a cardiac vector parameter of the first 3D object; and
control the user interface to simultaneously display the aligned first 3D object and the aligned second 3D object on a same axis,
wherein, upon receiving the control instruction from the processor, the user interface is configured to display the aligned first and second 3D objects for comparative analysis by a viewer.

2. The system of claim 1, wherein the first 3D object comprises a vector loop and the second 3D object is a vector loop.

3. The system of claim 1, wherein the first 3D object comprises a spatial QRS-T angle and the second 3D object is a spatial QRS-T angle.

4. The system of claim 1, wherein the first 3D object includes one or more of a QRS vector loop, a vector corresponding to a maximum of the QRS vector loop, a T vector loop, a vector corresponding to a maximum of the T vector loop, and a Q-RST angle between the vector corresponding to the maximum of the QRS vector loop and the vector corresponding to the maximum of the T vector loop, and
wherein the second 3D object includes one or more of a QRS vector loop, a vector corresponding to a maximum of the QRS vector loop, a T vector loop, a vector corresponding to a maximum of the T vector loop, and a Q-RST angle between the vector corresponding to the maximum of the QRS vector loop and the vector corresponding to the maximum of the T vector loop.

5. The system of claim 4, wherein the processor is further configured to execute the instructions to:
control the user interface to display two or more of an icon for viewing vector loops, an icon for viewing maximum vectors, and an icon for viewing QRS-T angle;
responsive to the user selecting the icon for viewing vector loops, control the user interface to display the QRS vector loop and T vector loop of the first 3D object and the second 3D object;
responsive to the user selecting the icon for viewing maximum vectors, control the user interface to display the maximum vectors of the first 3D object and the maximum vectors of the second 3D object, and
responsive to the user selecting the icon for viewing QRS-T angle, control the user interface to display the QRS-T angle for the first 3D object and the QRS-T angle for the second 3D object.

6. The system of claim 5, wherein the icon outputs are simultaneously displayed when multiple icons are selected.

7. The system of claim 1, wherein the processor is further configured to execute the instructions to determine a point of view showing a largest difference between the first 3D object and the second 3D object, wherein simultaneously displaying the first 3D object and the second 3D object comprising initially displaying the first 3D object and the second 3D object from the point of view.

8. The system of claim 1, wherein each of the cardiac vector parameter of the first 3D object and the cardiac vector parameter of the second 3D object comprise one of a maximum vector, a QRS axis, T axis, and P axis.

9. The system of claim 1, wherein the processor is further configured to execute the instructions to:

calculate a derivative of the vector loop of the first 3D object; and shade the vector loop of the first 3D object based on the calculated integral to show the vector gradient.

10. The system of claim 1, wherein the processor is further configured to execute the instructions to, responsive to a user input, change a point of view from which the first 3D object and the second 3D object are displayed.

11. A system for comparative analysis of cardiac information, the system comprising:

a user interface configured to provide information to a user and obtain information from a user;

a memory storing instructions; and a processor configured to execute the instructions to:

control the user interface to display a plurality of icons corresponding to three-dimensional (3D) objects, each 3D object being obtained from a different set of ECG data, each set of ECG data being obtained during a distinct time period;

control the user interface to display an xyz axis simultaneously with the plurality of icons; and responsive to selection of multiple icons, control the user interface to simultaneously display, on ax xyz axis, a first 3D object corresponding to a first icon and a second 3D object corresponding to a second icon such that the second 3D object is shifted to align with the first 3D object by aligning a cardiac vector parameter of the second 3D object with a cardiac vector parameter of the first 3D object, wherein, upon receiving the control instruction from the processor, the user interface is configured to display the aligned first and second 3D objects for comparative analysis by a viewer.

12. The system of claim 11, wherein the processor is further configured to execute the instructions to, responsive to deselection of an icon, control the user interface to remove a 3D object corresponding to the deselected icon from the xyz axis.

13. The system of claim 11, wherein each icon indicates a time at which a corresponding ECG measurement was taken.

14. The system of claim 11, wherein each of the cardiac vector parameter of the first 3D object and the cardiac vector parameter of the second 3D object comprise one of a maximum vector, a QRS axis, T axis, and P axis.

15. The system of claim 11, wherein the icons are ordered sequentially based on a time at which a corresponding ECG measurements were taken.

16. A method of displaying cardiac information, comprising:

obtaining a first set of ECG data, the first set of ECG data being measured from a patient during a first time period;

obtaining a second set of ECG data, the second set of ECG data being measured from the patient during a second time period distinct from the first time period;

obtaining a first three-dimensional (3D) object based on the first set of ECG data;

obtaining a second 3D object based on the second set of ECG data;

shift the second 3D object to align with the first 3D object by aligning a cardiac vector parameter of the second 3D object with a cardiac vector parameter of the first 3D object; and simultaneously displaying the aligned first 3D object and the aligned second 3D object on a same axis for comparative analysis by a viewer.

17. The method of claim 16, wherein the first 3D object comprises one or more of a vector loop spatial QRS-T angle and the second 3D object comprises one or more of a vector loop spatial QRS-T angle.

18. The method of claim 16, wherein the first 3D object includes one or more of a QRS vector loop, a vector corresponding to a maximum of the QRS vector loop, a T vector loop, a vector corresponding to a maximum of the T vector loop, and a Q-RST angle between the vector corresponding to the maximum of the QRS vector loop and the vector corresponding to the maximum of the T vector loop, and wherein the second 3D object includes one or more of a QRS vector loop, a vector corresponding to a maximum of the QRS vector loop, a T vector loop, a vector corresponding to a maximum of the T vector loop, and a Q-RST angle between the vector corresponding to the maximum of the QRS vector loop and the vector corresponding to the maximum of the T vector loop.

19. The method of claim 18, further comprising:

providing two or more of an icon for viewing vector loops, an icon for viewing maximum vectors, and an icon for viewing QRS-T angle;

responsive to the user selecting the icon for viewing vector loops, displaying the QRS vector loop and T vector loop of the first 3D object and the second 3D object, responsive to the user selecting the icon for viewing maximum vectors, displaying the maximum vectors of the first 3D object and the maximum vectors of the second 3D object, and responsive to the user selecting the icon for viewing QRS-T angle, displaying the QRS-T angle for the first 3D object and the QRS-T angle for the second 3D object.

20. The method of claim 16, further comprising:

obtaining a max QRS vector and a max T wave vector from the ECG data;

obtaining an integral of the max QRS vector and the max T-wave vector;

obtaining a ventricular gradient vector by summing of the integral of the max QRS vector and the integral of the max T vector; and displaying the ventricular gradient vector.

21. The method of claim 16, wherein the first set of ECG data is obtained from a measurement performed by from a first device and the second set of ECG data is obtained from a measurement performed by a second device.

22. The method of claim 16, wherein each of the cardiac vector parameter of the first 3D object and the cardiac vector parameter of the second 3D object comprise one of a maximum vector, a QRS axis, T axis, and P axis.

* * * * *